US012648897B2

(12) United States Patent
Blais et al.

(10) Patent No.: US 12,648,897 B2
(45) Date of Patent: Jun. 9, 2026

(54) COMPOSITION FOR THE SIMULTANEOUS BLEACHING AND DYEING OF KERATIN FIBRES AND PROCESS EMPLOYING THIS COMPOSITION

(71) Applicant: L'Oreal, Paris (FR)

(72) Inventors: Stéphane Blais, Aulnay-sous-Bois (FR); Stéphane Sabelle, Aulnay-sous-Bois (FR); Rahma Benni, Aulnay-sous-Bois (FR)

(73) Assignee: L'Oréal, Paris (FR)

(*) Notice: Subject to any disclaimer, the term of this patent is extended or adjusted under 35 U.S.C. 154(b) by 335 days.

(21) Appl. No.: 18/267,207

(22) PCT Filed: Dec. 16, 2021

(86) PCT No.: PCT/EP2021/086226

§ 371 (c)(1),
(2) Date: Jun. 14, 2023

(87) PCT Pub. No.: WO2022/129346

PCT Pub. Date: Jun. 23, 2022

(65) Prior Publication Data

US 2024/0058233 A1 Feb. 22, 2024

(30) Foreign Application Priority Data

Dec. 18, 2020 (FR) ...................................... 2013726

(51) Int. Cl.

| | |
|---|---|
| ***A61K 8/22*** | (2006.01) |
| ***A61K 8/19*** | (2006.01) |
| ***A61K 8/25*** | (2006.01) |
| ***A61Q 5/08*** | (2006.01) |
| ***A61Q 5/10*** | (2006.01) |

(52) U.S. Cl.

CPC .................. *A61K 8/22* (2013.01); *A61K 8/19* (2013.01); *A61K 8/25* (2013.01); *A61Q 5/08* (2013.01); *A61Q 5/10* (2013.01); *A61K 2800/432* (2013.01)

(58) Field of Classification Search

CPC ... A61K 8/22; A61K 8/19; A61K 8/25; A61K 2800/432; A61K 8/411; A61K 8/4946; A61K 2800/882; A61Q 5/08; A61Q 5/10; A61Q 5/065

See application file for complete search history.

(56) References Cited

U.S. PATENT DOCUMENTS

| | | | |
|---|---|---|---|
| 3,100,739 | A | 8/1963 | Kaiser et al. |
| 3,376,110 | A | 4/1968 | Shiraeff |
| 3,524,842 | A | 8/1970 | Grossmann et al. |
| 3,578,386 | A | 5/1971 | Kalopissis et al. |
| 3,617,163 | A | 11/1971 | Kalopissis et al. |
| 3,817,698 | A | 6/1974 | Kalopissis et al. |
| 3,869,454 | A | 3/1975 | Lang et al. |
| 3,955,918 | A | 5/1976 | Lang |
| 4,003,699 | A | 1/1977 | Rose et al. |
| 4,025,301 | A | 5/1977 | Lang |
| RE30,199 | E | 1/1980 | Rose et al. |
| 4,886,517 | A | 12/1989 | Bugaut et al. |
| 5,008,093 | A | 4/1991 | Merianos |
| 5,183,901 | A | 2/1993 | Login et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Möckli |
| 5,766,576 | A | 6/1998 | Löwe et al. |
| 5,879,413 | A | 3/1999 | Pengilly et al. |
| 5,888,252 | A | 3/1999 | Möckli |
| 5,919,273 | A | 7/1999 | Rondeau et al. |
| 5,944,360 | A | 8/1999 | Crapart |
| 5,993,490 | A | 11/1999 | Rondeau et al. |
| 6,045,591 | A | 4/2000 | Deneulenaere |
| 6,099,592 | A | 8/2000 | Vidal et al. |
| 6,136,042 | A | 10/2000 | Maubru |
| 6,179,881 | B1 | 1/2001 | Henrion et al. |
| 6,284,003 | B1 | 9/2001 | Rose et al. |
| 6,451,069 | B2 | 9/2002 | Matsunaga et al. |
| 6,458,167 | B1 | 10/2002 | Genet et al. |
| 6,730,789 | B1 | 5/2004 | Birault et al. |
| 6,797,013 | B1 | 9/2004 | Lang et al. |
| 6,863,883 | B1 | 3/2005 | Tsujino et al. |
| 7,833,290 | B2 | 11/2010 | Guerin et al. |
| 7,857,865 | B2 | 12/2010 | Guerin et al. |

(Continued)

FOREIGN PATENT DOCUMENTS

| | | | |
|---|---|---|---|
| DE | 2359399 | A1 | 6/1975 |
| DE | 2527638 | A1 | 5/1976 |

(Continued)

OTHER PUBLICATIONS

International Search Report and Written Opinion for counterpart Application No. PCT/EP2021/086226, dated Apr. 8, 2022.

(Continued)

*Primary Examiner* — Robert A Wax
*Assistant Examiner* — Kimberly Barber
(74) *Attorney, Agent, or Firm* — The Marbury Law Group, PLLC

(57) ABSTRACT

The present invention relates to a composition for simultaneous bleaching and dyeing of keratin fibres, comprising at least one chemical oxidizing agent, at least one (bi)carbonate, at least one silicate and at least one direct dye, and also to a process for simultaneous bleaching and dyeing of keratin fibres employing this composition.

20 Claims, No Drawings

(56) References Cited

U.S. PATENT DOCUMENTS

| | | | |
|---|---|---|---|
| 2009/0084395 A1 | 4/2009 | Glenn, Jr. et al. | |
| 2010/0154137 A1 | 6/2010 | Hercouet et al. | |
| 2016/0317413 A1 | 11/2016 | Lalleman et al. | |
| 2017/0333324 A1 | 11/2017 | Lalleman et al. | |
| 2017/0340549 A1 | 11/2017 | Anderheggen et al. | |
| 2020/0214942 A1 | 7/2020 | Haruki et al. | |

FOREIGN PATENT DOCUMENTS

| | | | |
|---|---|---|---|
| DE | 2538363 A1 | | 5/1976 |
| DE | 4133957 A1 | | 4/1993 |
| DE | 4137005 A1 | | 5/1993 |
| DE | 4220388 A1 | | 12/1993 |
| DE | 19543988 A1 | | 5/1997 |
| EP | 0714954 A2 | | 6/1996 |
| EP | 0770375 A1 | | 5/1997 |
| EP | 0850636 A1 | | 7/1998 |
| EP | 0850637 A1 | | 7/1998 |
| EP | 0860636 A1 | | 8/1998 |
| EP | 0918053 A1 | | 5/1999 |
| EP | 0920856 A1 | | 6/1999 |
| EP | 1062940 A1 | | 12/2000 |
| EP | 1133975 A2 | | 9/2001 |
| EP | 1133976 A2 | | 9/2001 |
| EP | 2191812 A1 | | 6/2010 |
| EP | 2702894 A1 | | 3/2014 |
| EP | 2723306 B1 | | 12/2016 |
| EP | 2702894 B1 | * | 1/2019 |
| EP | 3558218 B1 | * | 5/2022 |
| FR | 1567219 A | | 5/1959 |
| FR | 1221122 A | | 5/1960 |
| FR | 1516943 A | | 2/1968 |
| FR | 1540423 A | | 9/1968 |
| FR | 1560664 A | | 3/1969 |
| FR | 2189006 A1 | | 1/1974 |
| FR | 2275462 A1 | | 1/1976 |
| FR | 2285851 A1 | | 4/1976 |
| FR | 2570946 A1 | | 4/1986 |
| FR | 2733749 A1 | | 11/1996 |
| FR | 2757385 A1 | | 6/1998 |
| FR | 2788433 A1 | | 7/2000 |
| FR | 2801308 A1 | | 5/2001 |
| FR | 2886136 A1 | | 12/2006 |
| FR | 3060314 B1 | * | 8/2019 |
| GB | 738585 A | | 10/1955 |
| GB | 1026978 A | | 4/1966 |
| GB | 1153196 A | | 5/1969 |
| GB | 1163385 A | | 9/1969 |
| GB | 1195386 A | | 6/1970 |
| GB | 1514466 A | | 6/1978 |
| JP | 02-019576 A | | 1/1990 |
| JP | H04247016 A | | 9/1992 |
| JP | 05-163124 A | | 6/1993 |
| JP | H11246370 A | | 9/1999 |
| JP | 2002338444 A | | 11/2002 |
| JP | 2010143915 A | | 7/2010 |
| JP | 2010527732 A | | 8/2010 |
| JP | 2012236016 A | | 12/2012 |
| JP | 2013-213072 A | | 10/2013 |
| JP | 2019055941 A | | 4/2019 |
| WO | 94/08969 A1 | | 4/1994 |
| WO | 94/08970 A1 | | 4/1994 |
| WO | 95/01772 A1 | | 1/1995 |
| WO | 95/15144 A1 | | 6/1995 |
| WO | 96/15765 A1 | | 5/1996 |
| WO | 97/44004 A1 | | 11/1997 |
| WO | 99/48465 A1 | | 9/1999 |
| WO | 01/66646 A1 | | 9/2001 |
| WO | 03/029359 A1 | | 4/2003 |
| WO | 2008/152570 A1 | | 12/2008 |
| WO | 2015086677 A1 | | 6/2015 |
| WO | 2016/091814 A1 | | 6/2016 |
| WO | 2020020710 A1 | | 1/2020 |
| WO | 2022/129347 A1 | | 6/2022 |

OTHER PUBLICATIONS

International Search Report and Written Opinion for counterpart Application No. PCT/EP2021/086227, dated Apr. 19, 2022.

Mintel: "Londacolor Color Creme," Londa, Record ID 232927, XP055847971, Oct. 13, 2023.

Mintel: "Hair Colour," Londa, Record ID 574739, XP055847972, Aug. 23, 2006.

Alberti, G. et al., "Ricerche Sui Coloranti Cationici Per Fibra Acrilica," La Chimica E L'Industria, (Milan), (Sep. 1974), vol. 56, No. 9, pp. 600-603 (English translation unavailable).

Alberti, Guido et al., "Cationic Dyes Derived from Several Heterocyclic Amines with Two or More Heteroatoms," Annali di Chimica, (Rome), (1975), 65(5-6), pp. 305-314.

Albert, Guido et al., "Thermodynamic Features in Acrylic Fiber Dyeing with Basic Dyes," Textile Research Journal, (Feb. 1984), 54(2), pp. 105-107.

Balaban, Alexandru et al., "Reactions of Pyrylium Salts with Nucleophiles," Revue Roumaine de Chimie, (1998), 33(4), pp. 377-383.

Prostakov, N.S. et al., "2,5-Dimethyl-4-Nitroaryl (Aminoaryl) Pyridines in Synthesis," Chemistry and Chemical Technology, published by Ivanovo Chemical Technological Institute, vol. 22, No. 5, pp. 548-553 (no translation available).

Kuznetsova et al., "The determination of Thickness of a Histological Section by Interference Microscopy," Tsitologiya, vol. 10, No. 3, (1968), pp. 403-405.

Yen, Feng-Wen et al., "The Design and Synthesis of Bisazo Series Compound Used in Organophotoconductor," MRL Bull. Res. Dev., vol. 6, No. 2 (1992), pp. 21-27.

Neidlein, Richard et al., "Synthese von Substituierten Pyridiniumsalzen," German Monatshefte für Chemie, (1975), vol. 106, No. 3, pp. 643-648 (English translation unavailable).

Savarino et al., "Disperse and Cationic Dyes from Aminophenyl-X-Azolo-Pyridines," Dhes and Pigments, vol. 11, (1989), pp. 163-172.

Seidler, Von Eberhard et al., "Die Eignung Verschiedener Ditetrazoliumsalze als Reduktionsindikatoren in der Enzymhistochemie," Acta histochem. Bd. 61 (1), 1978, pp. 48-52. (The qualification of different diterazolium salts as indicators in the oxido-reductase histochemistry).

Stashkevich, et al., The Journal of General Chemistry of the USSR (translated from Russian), vol. 40(1), pp. 178-183 (English translation of Zh. Obshch. Khim., vol. 40(1), (1970), pp. 195-202.

Tien, Hsien-Ju et al., "Syntheses of New Azo Dyestuff Containing a Sydnone Ring," Journal of the Chinese Chemical Society, (Taipei), (1998), 45(1), pp. 209-211.

Viscardi, Guido et al., "Disperse Cationic Azo Dyes from Heterocyclic Intermidiates," Dyes and Pigments, vol. 19, No. 1, (1992), pp. 69-79.

Zhousheng, Y., "Research and Application of the Coordination Reaction of New Fluorescent Reagent CCPAR and CU (II)," Lihua_Jianyan_Huaxue_Fence_vol. 29_No. 4_1993_pp. 233-4.

Notice of Reasons for Refusal in JP2023537141, dated Jul. 16, 2024, 6 pages.

Notice of Reasons for Refusal in JP2023537144, dated Jul. 29, 2024, 12 pages.

Non-Final Office Action for copending U.S. Appl. No. 18/267,209, dated Nov. 4, 2024.

Final Office Action for copending U.S. Appl. No. 18/267,209, dated Mar. 11, 2025.

* cited by examiner

COMPOSITION FOR THE SIMULTANEOUS BLEACHING AND DYEING OF KERATIN FIBRES AND PROCESS EMPLOYING THIS COMPOSITION

CROSS REFERENCE TO RELATED APPLICATIONS

This is a National Stage Application of PCT/EP2021/086226, filed internationally on Dec. 16, 2021, which claims priority to French Application No. 2013726, filed on Dec. 18, 2020, both of which are incorporated by reference herein in their entireties.

TECHNICAL FIELD OF THE INVENTION

The present invention relates to a composition for simultaneous bleaching and dyeing of keratin fibres, comprising at least one chemical oxidizing agent, at least one (bi) carbonate, at least one silicate and at least one direct dye, and also to a process for simultaneous bleaching and dyeing of keratin fibres employing this composition.

BACKGROUND OF THE INVENTION

When a person wishes to radically change hair colour, in particular when he or she wishes to obtain a lighter colour than his or her original colour, it is often necessary to carry out bleaching and then dyeing of the hair. Several methods exist for doing this. The first method consists in using lightening products based on aqueous ammonia and on hydrogen peroxide. These products can optionally contain dyes which makes it possible to simultaneously lighten and dye the hair. However, the lightening performance results of these products remain limited, more particularly for applications to natural and/or dyed dark-coloured hair.

The second method consists in applying to the hair lightening compositions based on peroxygenated salts, such as persulfates, and on alkaline agents, to which compositions hydrogen peroxide has been added at the time of use, in order to obtain greater lightening. However, these bleaching treatments are generally accompanied by the appearance of unattractive orange-yellow glints. In order to overcome this problem, these compositions can comprise direct dyes making it possible to simultaneously bleach and dye the hair with the aim of obtaining a more aesthetic colour result.

However, the range of direct dyes that can be used in these compositions remains restricted since only stable direct dyes can be used under such conditions in order to obtain good build-up of the colouring and intense and chromatic colours. In order to attempt to overcome this stability problem, it has been envisaged to carry out the process in two stages: a first stage during which the hair is bleached using the lightening composition and then a second stage during which the hair is dyed using a composition comprising direct dyes. However, a two-stage process is not satisfactory since, in addition to creating numerous handling procedures, it exhibits the disadvantage of being relatively long and can result in a greater deterioration in the quality of the fibre.

There thus exists a real need to develop a composition for simultaneous bleaching and dyeing of keratin fibres comprising direct dyes, the composition having both good lightening properties and good dyeing properties, particularly when it is applied to dark-coloured hair, and making it possible in particular to obtain good build-up of the colouring and also intense and chromatic colours. Furthermore, such a composition can comprise a wide range of direct dyes making it possible to obtain the shade sought by the user. Finally, such a composition can be used in a single-stage process for simultaneous bleaching and dyeing of keratin fibres. Such a composition should also be more respectful of the quality of the fibres.

The applicant has discovered, surprisingly, that all of these objectives can be achieved by the composition according to the present invention.

SUMMARY OF THE INVENTION

According to a first aspect, a subject-matter of the present invention is a composition comprising:

i) one or more chemical oxidizing agents chosen from hydrogen peroxide, hydrogen peroxide-generating systems other than peroxygenated salts and their mixtures;

ii) one or more compounds chosen from carbonates, carbonate-generating systems, bicarbonates, bicarbonate-generating systems and their mixtures;

iii) one or more silicates;

iv) one or more direct dyes;

wherein the composition comprises a content of persulfates of less than 10% by weight.

According to a second aspect, a subject-matter of the present invention is a process for simultaneous bleaching and dyeing of keratin fibres comprising the application, to the keratin fibres, of a composition as defined above.

According to a third aspect, a subject-matter of the present invention is the use of a composition as defined above for the simultaneous bleaching and dyeing of keratin fibres.

According to a fourth aspect, a subject-matter of the present invention is a multi-compartment device (kit) comprising:

a first compartment including a composition (A) comprising i) one or more chemical oxidizing agents chosen from hydrogen peroxide, hydrogen peroxide-generating systems other than peroxygenated salts and their mixtures; and a second compartment including a composition (B1) comprising:

ii) one or more compounds chosen from carbonates, carbonate-generating systems, bicarbonates, bicarbonate-generating systems and their mixtures; and iii) one or more silicates; and iv) one or more direct dyes;

or a first compartment containing a composition (A) comprising i) one or more chemical oxidizing agents chosen from hydrogen peroxide, hydrogen peroxide-generating systems other than peroxygenated salts and their mixtures; and a second compartment including a composition (B2) comprising:

ii) one or more compounds chosen from carbonates, carbonate-generating systems, bicarbonates, bicarbonate-generating systems and their mixtures; and iii) one or more silicates; and a third compartment including a composition (C) comprising iv) one or more direct dyes.

DETAILED DESCRIPTION OF THE INVENTION

Within the meaning of the present invention and unless otherwise indicated:

- the term "keratin fibres" is understood to mean fibres of human or animal origin, such as head hair, body hairs, the eyelashes, the eyebrows, wool, angora, cashmere or fur.

According to the present invention, the keratin fibres are preferably human keratin fibres, more preferentially the hair, even more preferentially the head hair.

- the term "alkyl group" is understood to mean a saturated, linear or branched, hydrocarbon radical;
- the term "($C_x$-$C_y$)alkyl group" is understood to mean an alkyl group comprising from x to y carbon atoms;
- the term "silicate" is understood to mean a silicic acid salt;
- the term "oxidation dye" is understood to mean an oxidation dye precursor chosen from oxidation bases and couplers. Oxidation bases and couplers are colourless or sparingly coloured compounds, which, via a condensation reaction in the presence of an oxidizing agent, give a coloured entity;
- the term "direct dye" is understood to mean a natural and/or synthetic dye, including in the form of extract(s), other than oxidation dyes. They are coloured compounds which will spread superficially over the fibre. They can be ionic or non-ionic, i.e. anionic, cationic, neutral or non-ionic;
- the term "chemical oxidizing agent" is understood to mean an oxidizing agent other than atmospheric oxygen;
- the term "(bi)carbonate" is understood to mean a carbonate or a bicarbonate.

Unless otherwise indicated, when compounds are mentioned in the present patent application, this is also understood to mean their optical isomers, their geometrical isomers, their tautomers, their salts, their solvates, such as hydrates, and their mixtures.

The expressions "at least one" and "one or more" are synonymous and can be used interchangeably.

The expressions "lightening" and "bleaching" are synonymous and can be used interchangeably.

Composition

According to a first aspect, a subject-matter of the present invention is a composition as defined above.

The applicant has noted, surprisingly, that the composition according to the present invention makes it possible to stabilize the direct dye(s) and to obtain a satisfactory level of lightening and also better build-up of the colouring and intense and chromatic colours. Moreover, the composition according to the invention is more respectful of the quality of the fibres, minimizing in particular their deterioration.

Finally, the composition according to the invention can be used in a single-stage process for simultaneous bleaching and dyeing of keratin fibres.

According to a preferred embodiment, the composition according to the invention comprises:

- i) hydrogen peroxide;
- ii) one or more compounds chosen from carbonates, bicarbonates and their mixtures;
- iii) one or more silicates;
- iv) one or more direct dyes;
- wherein the composition comprises a content of persulfates of less than 10% by weight.

Chemical Oxidizing Agents

The composition according to the invention comprises i) one or more chemical oxidizing agents chosen from hydrogen peroxide, hydrogen peroxide-generating systems other than peroxygenated salts and their mixtures.

The hydrogen peroxide-generating systems other than peroxygenated salts can be chosen from urea hydrogen peroxide, polymeric complexes which can release hydrogen peroxide, oxidases and their mixtures.

Mention may be made, by way of example of polymeric complexes which can release hydrogen peroxide, of polyvinylpyrrolidone/$H_2O_2$, in particular which is provided in the powder form, and the other polymeric complexes described in U.S. Pat. Nos. 5,008,093, 3,376,110 and 5,183,901.

Oxidases can produce hydrogen peroxide in the presence of a suitable substrate, such as, for example, glucose in the case of glucose oxidase or uric acid with uricase.

According to a specific embodiment, the hydrogen peroxide and/or the hydrogen peroxide-generating system(s) other than peroxygenated salts can be added to the composition according to the invention just before it is applied to the keratin fibres. The intermediate composition(s) comprising hydrogen peroxide and/or hydrogen peroxide-generating system(s) other than peroxygenated salts can be referred to as oxidizing compositions and can also include various additional compounds or various adjuvants conventionally used in compositions for the dyeing of keratin fibres.

According to a preferred embodiment, the composition according to the invention comprises hydrogen peroxide as chemical oxidizing agent.

The chemical oxidizing agent(s) are preferably present in a total content ranging from 1% to 12% by weight, more preferentially ranging from 3% to 9% by weight, more preferentially still ranging from 3.5% to 8.5% by weight, with respect to the total weight of the composition.

According to a preferred embodiment, the hydrogen peroxide is present in a total content ranging from 1% to 12% by weight, preferably ranging from 3% to 9% by weight, more preferentially ranging from 3.5% to 8.5% by weight, with respect to the total weight of the composition.

(Bi)Carbonates and/or (Bi)Carbonate-Generating Systems

The composition according to the invention additionally comprises ii) one or more compounds chosen from carbonates, carbonate-generating systems, bicarbonates, bicarbonate-generating systems and their mixtures.

According to a preferred embodiment, the composition according to the invention additionally comprises ii) one or more compounds chosen from carbonates, bicarbonates and their mixtures.

According to a more preferred embodiment, the composition according to the invention additionally comprises ii) one or more compounds chosen from ammonium carbonate, ammonium bicarbonate and their mixtures.

The compound(s) ii) are preferably present in a total content ranging from 0.01% to 20% by weight, more preferentially ranging from 1% to 15% by weight, more preferentially still ranging from 2% to 15% by weight, most preferentially ranging from 4% to 15% by weight, with respect to the total weight of the composition.

Carbonates and/or Carbonate-Generating Systems

The term "carbonate-generating system" is understood to mean a system which generates the carbonate in situ, such as, for example, carbon dioxide in water or percarbonate in water.

Preferably, the carbonate(s) are chosen from:

- alkali metal carbonates;
- alkaline earth metal carbonates;

lanthanide carbonates;
transition metal carbonates;
bismuth carbonate;
cadmium carbonate;
thallium carbonate;
zinc carbonate;
the compounds of formula $(N^+R^1R^2R^3R^4)_2CO_3^{2-}$ wherein $R^1$, $R^2$, $R^3$ and $R^4$ represent, independently of one another, a hydrogen atom or a $(C_1$-$C_4)$alkyl group optionally substituted by a hydroxyl group;
guanidine carbonate;
their mixtures.

More preferentially, the carbonate(s) are chosen from sodium carbonate, potassium carbonate, caesium carbonate, lithium carbonate, magnesium carbonate, calcium carbonate, barium carbonate, strontium carbonate, cerium carbonate, lanthanum carbonate, yttrium carbonate, copper(II) carbonate, manganese carbonate, nickel carbonate, silver carbonate, zirconium carbonate, bismuth carbonate, cadmium carbonate, thallium carbonate, zinc carbonate, ammonium carbonate, guanidine carbonate, tetraethylammonium carbonate and their mixtures.

More preferentially still, the carbonate(s) are chosen from sodium carbonate, potassium carbonate, caesium carbonate, magnesium carbonate, calcium carbonate, cerium carbonate, manganese carbonate, zinc carbonate, ammonium carbonate, guanidine carbonate and their mixtures.

Most preferentially, the carbonate(s) are chosen from sodium carbonate, potassium carbonate, magnesium carbonate, calcium carbonate, ammonium carbonate and their mixtures.

According to a particularly preferred embodiment, the carbonate included in the composition is ammonium carbonate.

The carbonate(s) and/or the carbonate-generating system(s) are preferably present in a total content ranging from 0.01% to 20% by weight, more preferentially ranging from 1% to 15% by weight, more preferentially still ranging from 2% to 15% by weight, most preferentially ranging from 4% to 15% by weight, with respect to the total weight of the composition.

According to a preferred embodiment, the carbonate(s) are present in a total content ranging from 0.01% to 20% by weight, preferably ranging from 1% to 15% by weight, more preferentially ranging from 2% to 15% by weight, more preferentially still ranging from 4% to 15% by weight, with respect to the total weight of the composition.

According to a preferred embodiment, the compound(s) ii) are chosen from carbonates, carbonate-generating systems and their mixtures, preferably from carbonates.

Bicarbonates and/or Bicarbonate-Generating Systems

The term “bicarbonate-generating system” is understood to mean a system which generates the bicarbonate in situ, such as, for example, carbon dioxide in water or by buffering a carbonate with an inorganic or organic acid.

Preferably, the bicarbonate(s) are chosen from:
alkali metal bicarbonates;
alkaline earth metal bicarbonates;
the compounds of formula $N^+R^1R^2R^3R^4HCO_3^-$ wherein $R^1$, $R^2$, $R^3$ and $R^4$ represent, independently of one another, a hydrogen atom or a $(C_1$-$C_4)$alkyl group optionally substituted by a hydroxyl group;
aminoguanidine bicarbonate;
their mixtures.

More preferentially, the bicarbonate(s) are chosen from sodium bicarbonate, potassium bicarbonate, lithium bicarbonate, caesium bicarbonate, calcium bicarbonate, magnesium bicarbonate, ammonium bicarbonate, choline bicarbonate, triethylammonium bicarbonate, aminoguanidine bicarbonate and their mixtures.

More preferentially still, the bicarbonate(s) are chosen from sodium bicarbonate, potassium bicarbonate, caesium bicarbonate, calcium bicarbonate, magnesium bicarbonate, ammonium bicarbonate and their mixtures.

Most preferentially, the bicarbonate(s) are chosen from sodium bicarbonate, potassium bicarbonate, ammonium bicarbonate and their mixtures.

According to a particularly preferred embodiment, the bicarbonate included in the composition is ammonium bicarbonate.

The bicarbonates can originate from a natural water, for example spring water from the Vichy basin or from La Roche Posay or Badoit water.

The bicarbonate(s) and/or the bicarbonate-generating system(s) are preferably present in a total content ranging from 0.01% to 20% by weight, more preferentially ranging from 1% to 15% by weight, more preferentially still ranging from 2% to 15% by weight, most preferentially ranging from 4% to 15% by weight, with respect to the total weight of the composition.

According to a preferred embodiment, the bicarbonate(s) are present in a total content ranging from 0.01% to 20% by weight, preferably ranging from 1% to 15% by weight, more preferentially ranging from 2% to 15% by weight, more preferentially still ranging from 4% to 15% by weight, with respect to the total weight of the composition.

According to a preferred embodiment, the compound(s) ii) are chosen from bicarbonates, bicarbonate-generating systems and their mixtures, preferably from bicarbonates.

Silicates

The composition according to the invention additionally comprises iii) one or more silicates.

The silicate(s) are preferably water-soluble.

The term “water-soluble silicate” is understood to mean a silicate which exhibits a solubility in water at ordinary ambient temperature (25° C.) and at atmospheric pressure (760 mmHg) of greater than 0.5% by weight, preferably of greater than 1% by weight.

Preferably, the silicate(s) are chosen from alkali metal silicates, alkaline earth metal silicates, aluminium silicates, trimethylammonium silicates and their mixtures.

More preferentially, the silicate(s) are chosen from sodium silicates, potassium silicates, calcium silicates, aluminium silicates, trimethylammonium silicates and their mixtures.

More preferentially still, the silicate(s) are chosen from sodium silicates. Mention may be made, by way of example of sodium silicates, of compounds having the CAS numbers: [1344-09-8] and [6834-92-0].

The silicate(s) are preferably present in a total content ranging from 1% to 40% by weight, more preferentially ranging from 2% to 35% by weight, more preferentially still ranging from 3% to 35% by weight, most preferentially ranging from 4% to 20% by weight, with respect to the total weight of the composition.

The total amount of (bi)carbonate(s) and/or (bi)carbonate-generating system(s) ii)/total amount of silicate(s) iii) ratio by weight is preferably from 0.00025 to 2000, more preferentially from 0.06 to 15, more preferentially still from 1 to 7.5.

According to a preferred embodiment, the total amount of (bi)carbonate(s) ii)/total amount of silicate(s) iii) ratio by weight is from 0.00025 to 2000, preferably from 0.06 to 15, more preferentially from 1 to 7.5.

The total amount of (bi)carbonate(s) and/or (bi)carbonate-generating system(s) ii)/total amount of chemical oxidizing agent(s) i) ratio by weight is preferably from 0.0008 to 20, more preferentially from 0.1 to 5, more preferentially still from 0.2 to 4.3.

According to a preferred embodiment, the total amount of (bi)carbonate(s) ii)/total amount of chemical oxidizing agent(s) i) ratio by weight is from 0.0008 to 20, preferably from 0.1 to 5, more preferentially from 0.2 to 4.3.

According to a more preferred embodiment, the total amount of (bi)carbonate(s) ii)/total amount of hydrogen peroxide ratio by weight is from 0.0008 to 20, preferably from 0.1 to 5, more preferentially from 0.2 to 4.3.

The total amount of carbonate(s) and/or carbonate-generating system(s)/total amount of bicarbonate(s) and/or bicarbonate-generating system(s) ratio by weight is preferably from 0.01 to 100, more preferentially from 0.01 to 1, more preferentially still from 0.01 to 0.75.

According to a preferred embodiment, the total amount of carbonate(s)/total amount of bicarbonate(s) ratio by weight is from 0.01 to 100, preferably from 0.01 to 1, more preferentially from 0.01 to 0.75.

The composition preferably comprises a total content of magnesium carbonate of less than 5% by weight, more preferentially of less than 1% by weight, more preferentially still of less than 0.1% by weight, most preferentially of less than 0.01% by weight and better still of less than 0.001% by weight.

According to a particularly preferred embodiment, the composition is devoid of magnesium carbonate.

The composition comprises a total content of persulfates of less than 10% by weight, preferably of less than 5% by weight, more preferentially of less than 1% by weight, more preferentially still of less than 0.1% by weight, most preferentially of less than 0.01% by weight and better still of less than 0.001% by weight.

According to a particularly preferred embodiment, the composition is devoid of persulfates.

Direct Dyes

The composition according to the invention additionally comprises iv) one or more direct dyes.

The direct dye(s) can be chosen from neutral, cationic or anionic direct dyes and their mixtures.

The direct dyes can be neutral, cationic or anionic direct dyes chosen from: acridines; acridones; anthranthrones; anthrapyrimidines; anthraquinones; azines; (poly)azos or azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bis-isoindolines; carboxanilides; coumarins; cyanines, such as (di)azacarbocyanines, (di)azahemicyanines, hemicyanines or tetraazacarbocyanines; (di)azines; bis-azines; (di)oxazines; (di)thiazines; (di) phenylamines; (di)phenylmethanes; (di)ketopyrrolopyrroles; flavonoids, such as flavanthrones and flavones; fluorindines; formazans; indamines; indanthrones; indigoids, thioindigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, in particular nitro(hetero) aromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazolines; thiazines; thiopyronines; triarylmethanes or xanthenes and natural direct dyes. Preferably, the direct dyes are chosen from anthraquinones, (poly)azos, azomethines and stilbenes, more preferentially from anthraquinones.

The direct dyes can be chosen in particular from neutral, cationic or anionic nitrobenzene direct dyes, neutral, cationic or anionic azo direct dyes, neutral, cationic or anionic tetraazapentamethine dyes, cationic or anionic quinone dyes and in particular neutral, cationic or anionic anthraquinone dyes, neutral, cationic or anionic azine direct dyes, neutral, cationic or anionic triarylmethane direct dyes, neutral, cationic or anionic azomethine direct dyes and natural direct dyes. Preferably, the direct dyes are chosen from neutral or anionic anthraquinone dyes and stilbenes.

Mention may be made, by way of neutral, anionic or cationic direct dyes which can be used in the present invention, of the following dyes: acridines; acridones; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines, such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids, such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, in particular nitro(hetero)aromatics; oxadiazoles; oxazines; perilones; perinones; perylenes; phenazines; phenoxazine; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazoles; thiazines; thioindigo; thiopyronines; triarylmethanes or xanthenes.

Neutral Direct Dyes

The direct dyes can be neutral direct dyes, preferably chosen from the hydrazono dyes of formulae (IIIa) and (III'a), the azo and styryl dyes (IVa), the diazo and distyryl dyes (IV'a) and (IV"a), the anthraquinone dyes (Va) and the azomethine dyes (VIa) and (VI'a) below, and their mixtures:

$$Ar''-C(R^a)=N-N(R^b)-Ar \quad (IIIa)$$

$$Ar''-N(R^a)-N=C(R^b)-Ar \quad (III'a)$$

$$Ar-T=T'-Ar'' \quad (IVa)$$

$$Ar''-T=T'-Ar'-T'=T-Ar \quad (IV'a)$$

$$Ar-T=T'-L-T'=T-Ar \quad (IV''a)$$

(Va)

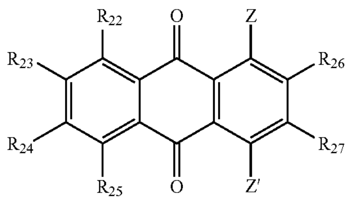

-continued (VIa)

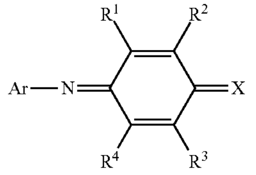

(VI'a)

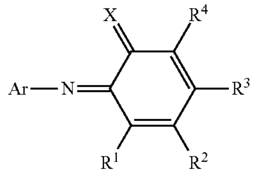

in which formulae (IIIa), (III'a), (IVa), (IV'a), (IV"a), (Va), (VIa) and (VI'a):

Ar represents an aryl group, such as phenyl or naphthyl, substituted by at least one electron-donating group, such as i) optionally substituted $(C_1-C_8)$alkyl, ii) optionally substituted $(C_1-C_8)$alkoxy, iii) (di)$(C_1-C_8)$(alkyl)amino optionally substituted on the alkyl group(s) by a hydroxyl group, iv) aryl$(C_1-C_8)$alkylamino, v) optionally substituted N—$(C_1-C_8)$alkyl-N-aryl$(C_1-C_8)$alkylamino or Ar represents a julolidine group;

Ar' represents an optionally substituted divalent (hetero) arylene group, such as phenylene, particularly para-phenylene, or naphthalene, which is optionally substituted, preferably by one or more $(C_1-C_8)$alkyl, hydroxyl or $(C_1-C_8)$alkoxy group(s);

Ar" represents a (hetero)aryl group which is optionally substituted, preferably by at least i) an electron-withdrawing group, such as nitro, nitroso or —C(X)—X'—R', or ii) a (di)$(C_1-C_6)$(alkyl)amino group, iii) a hydroxyl group or iv) a $(C_1-C_6)$alkoxy group; (hetero) aryl is particularly chosen from imidazolyl, triazolyl, indolyl or pyridyl or phenyl optionally substituted by at least one group chosen from nitro, nitroso and amino, preferably substituted in the para position of the phenyl group;

X, X' and X", which are identical or different, represent an oxygen or sulfur atom or an NR" group, preferably an oxygen atom;

$R^1$, $R^2$, $R^3$ and $R^4$, which are identical or different, represent a hydrogen or halogen atom, or a group chosen from hydroxyl, thiol, $(C_1-C_4)$alkyl, $(C_1-C_4)$alkoxy, (di)$(C_1-C_4)$(alkyl)amino, nitro and nitroso;

R' and R" represent a $(C_1-C_4)$alkyl group;

$R^a$ and $R^b$, which are identical or different, represent a hydrogen atom or a $(C_1-C_8)$alkyl group, which is optionally substituted, preferably by a hydroxyl group;

or, in an alternative form, the substituent $R^a$ with a substituent of Ar" and/or $R^b$ with a substituent of Ar and/or $R^a$ with $R^b$ form, together with the atoms which carry them, a (hetero)cycloalkyl;

in particular, $R^a$ and $R^b$ represent a hydrogen atom or a $(C_1-C_4)$alkyl group which is optionally substituted by a hydroxyl group;

T and T', which are identical or different, represent a $C(R^a)$ group or N, preferably N; and L represents a divalent group -ALK—, —C(X)-ALK—, -ALK-C(X)— or —C(X)-ALK-C(X')—, with ALK representing a linear or branched $(C_1-C_6)$alkylene group, such as methylene, and X and X' as defined above;

$R_{22}$, $R_{23}$, $R_{24}$, $R_{25}$, $R_{26}$ and $R_{27}$, which are identical or different, represent a hydrogen or halogen atom or a group chosen from:

$(C_1-C_6)$alkyl;

hydroxyl, mercapto;

$(C_1-C_6)$alkoxy, $(C_1-C_6)$alkylthio;

aryloxy or arylthio;

aryl$(C_1-C_6)$(alkyl)amino;

(di)$(C_1-C_6)$(alkyl)amino;

(di)(hydroxy$(C_1-C_6)$alkyl)amino;

Z' represents a hydrogen atom or an $NR_{28}R_{29}$ group with $R_{28}$ and $R_{29}$, which are identical or different, representing a hydrogen atom or a group chosen from:

$(C_1-C_6)$alkyl;

polyhydroxy$(C_1-C_6)$alkyl, such as hydroxyethyl;

aryl optionally substituted by one or more group(s), particularly i) $(C_1-C_6)$alkyl; iii) R°—C(X)—X'—, R°—X'—C(X)— or R°—X'—C(X)—X"— with R° representing a $(C_1-C_6)$alkyl group and X, X' and X" as defined above; iv) a sulfonate;

cycloalkyl; in particular cyclohexyl;

Z represents a group chosen from hydroxyl and $NR'_{28}R'_{29}$ with $R'_{28}$ and $R'_{29}$, which are identical or different, representing the same atoms or groups as $R_{28}$ and $R_{29}$ as defined above.

The direct dyes of formula (IV"a) are preferably of formula (IV'"a)

(IV'"a)

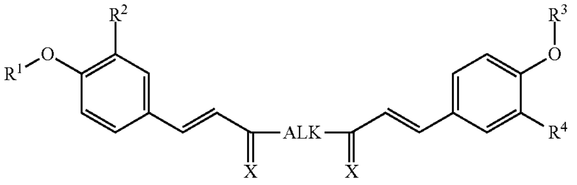

in which formula (IV'"a):

$R^1$ and $R^3$, which are identical or different, preferably identical, represent a hydrogen atom, a $(C_1-C_4)$alkyl group, such as methyl, or a sugar group, such as glucosyl, preferably a hydrogen atom;

$R^2$ and $R^4$, which are identical or different, preferably identical, represent a hydrogen atom, a $(C_1-C_4)$alkyl or $(C_1-C_4)$alkoxy group or an —O-sugar group, such as —O-glucosyl, preferably a $(C_1-C_4)$alkoxy group, such as methoxy;

X, which are identical or different, preferably identical, represent an oxygen or sulfur atom or N—R with R representing a hydrogen atom or a group, preferably an oxygen atom;

ALK represents a $(C_1-C_4)$alkylene group, such as methylene or ethylene, preferably methylene.

The direct dyes of formula (IV"a) can result from curcumin, demethoxycurcumin and bis-demethoxycurcumin.

Preferably, the direct dyes are chosen from the direct dyes of formulae (IV"a) and (IV'"a) and their mixtures as defined above.

According to a particularly preferred embodiment, the direct dyes are neutral direct dyes chosen from the following compounds (A) to (G) and their mixtures:

(A)

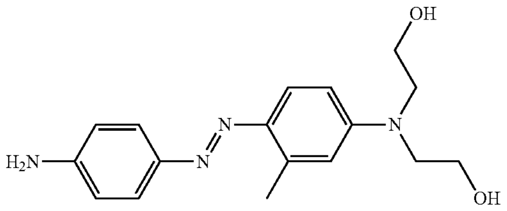

(B)

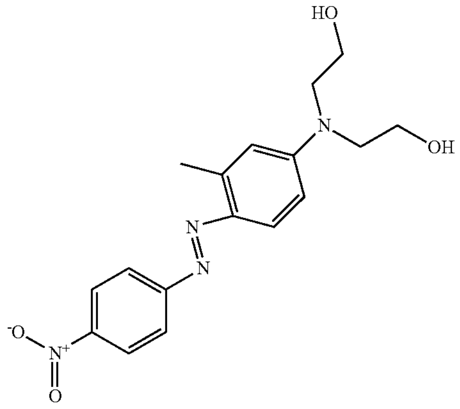

(C)

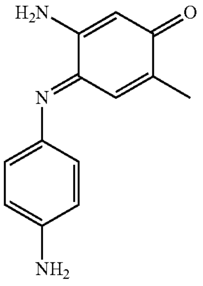

(D)

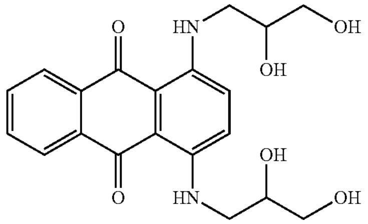

(E)

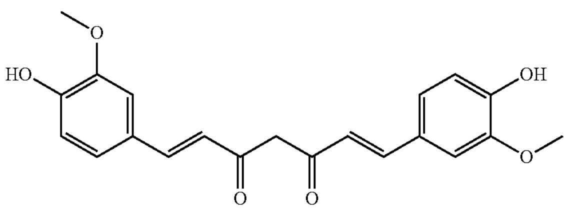

(F)

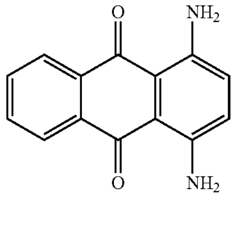

-continued (G)

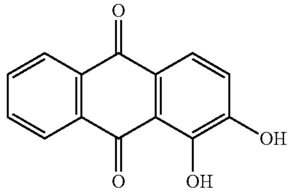

preferably from the compounds (E), (F) and (G) and their mixtures, more preferentially from the compounds (E) and (G) and their mixtures.

Cationic Direct Dyes

The direct dyes can be chosen from direct dyes which are cationic or commonly referred to as “basic dyes” for their affinity with acidic substances comprising in particular in their structure at least one endo- or exocyclic cationic or cationizable group.

Mention may in particular be made, as cationic azo dyes which can be used in the present invention, of the cationic dyes described in the Kirk-Othmer Encyclopedia of Chemical Technology, “Dyes, Azo”, J. Wiley & Sons, updated on 19 Apr. 2010.

Mention may also be made of the cationic azo dyes described in Patent Applications WO 95/15144, WO 95/01772 and EP 714 954.

Mention may also be made of the cationic azo dyes described in the Colour Index International, 3rd Edition, in particular of the following compounds: Basic Red 22, Basic Red 76, Basic Yellow 57, Basic Brown 16 and Basic Brown 17.

Among the cationic quinone dyes, those mentioned in the Colour Index International, 3rd Edition, are suitable and mention may be made, among these, inter alia, of the following dyes: Basic Blue 22 and Basic Blue 99.

Mention may be made, among the azine dyes which are suitable, of those listed in the Colour Index International, 3rd edition, and for example of the following dyes: Basic Blue 17 and Basic Red 2.

Mention may be made, among the cationic triarylmethane dyes which can be used according to the invention, besides those listed in the Colour Index International, 3rd Edition, of the following dyes: Basic Green 1, Basic Violet 3, Basic Violet 14, Basic Blue 7 and Basic Blue 26.

Mention may also be made of the direct dyes in the documents U.S. Pat. No. 5,888,252, EP 1 133 975, WO 03/029359, EP 860 636, WO 95/01772, WO 95/15144 and EP 714 954. Mention may also be made of those listed in the encyclopedia “The Chemistry of Synthetic Dyes” by K. Venkataraman, 1952, Academic Press, Vol. 1 to 7, in the “Kirk-Othmer Encyclopedia of Chemical Technology”, in the chapter “Dyes and Dye Intermediates”, 1993, Wiley & Sons, and in various chapters of “Ullmann’s Encyclopedia of Industrial Chemistry”, 7th edition, Wiley & Sons.

Preferably, the cationic direct dyes are chosen from those resulting from dyes of azo and hydrazono type.

The cationic direct dyes can be cationic azo dyes, as described in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. Nos. 3,524,842, 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

Preferably, the cationic direct dyes comprise a quaternary ammonium group; more preferentially, the cationic charge is endocyclic. These cationic groups are, for example, a cationic group:

having an exocyclic (di/tri)($C_1$-$C_8$)alkylammonium charge, or having an endocyclic charge, such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the cationic hydrazono direct dyes of formulae (IIb) and (IIIb) and the cationic azo direct dyes of formulae (IVb) and (Vb) below:

$Het^+—C(R_a)═N—N(R_b)—ArQ^-$ (IIb);

$Het^+—N(R_a)—N═C(R_b)—ArQ^-$ (IIIb);

$Het^+—N═N—ArQ^-$ (IVb);

$Ar^+—N═N—Ar''Q^-$ (Vb);

in which formulae (IIb) to (Vb):

$Het^+$ represents a cationic heteroaryl group, preferentially having an endocyclic cationic charge, such as imidazolium, indolium or pyridinium, which is optionally substituted, preferentially by at least one ($C_1$-$C_8$)alkyl group, such as methyl;

$Ar^+$ represents an aryl group, such as phenyl or naphthyl, having an exocyclic cationic charge, preferentially ammonium, particularly tri($C_1$-$C_8$)alkylammonium, such as trimethylammonium;

Ar represents an aryl group, in particular phenyl, which is optionally substituted, preferentially by one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) by a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar'' represents an optionally substituted (hetero)aryl group, such as phenyl or pyrazolyl, which are optionally substituted, preferentially by one or more ($C_1$-$C_8$) alkyl, hydroxyl, (di)($C_1$-$C_8$)(alkyl)amino, ($C_1$-$C_8$) alkoxy or phenyl groups;

$R_a$ and $R_b$, which are identical or different, represent a hydrogen atom or a ($C_1$-$C_8$)alkyl group which is optionally substituted, preferentially by a hydroxyl group;

or else the substituent $R_a$ with a substituent of $Het^+$ and/or $R_b$ with a substituent of Ar and/or $R_a$ with $R_b$ form, together with the atoms which carry them, a (hetero) cycloalkyl; in particular, $R_a$ and $R_b$ represent a hydrogen atom or a ($C_1$-$C_4$)alkyl group optionally substituted by a hydroxyl group;

$Q^-$ represents an anionic counterion, such as a halide, an alkyl sulfate or an alkylsulfonate.

In particular, mention may be made of the azo and hydrazono direct dyes having an endocyclic cationic charge of formulae (IIb) to (Vb) as defined above. More particularly, mention may be made of the cationic direct dyes of formulae (IIb) to (Vb) having an endocyclic cationic charge described in Patent Applications WO 95/15144, WO 95/01772 and EP 714 954.

Preferably, mention may be made of the following direct dyes:

(II-1)

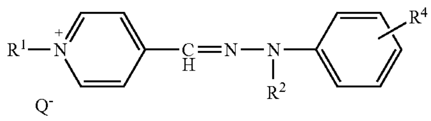

(IV-1)

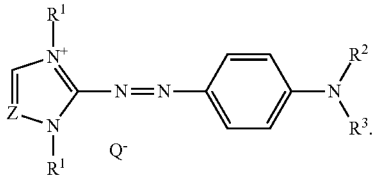

in which formulae (II-1) and (IV-1):

$R^1$ represents a ($C_1$-$C_4$)alkyl group, such as methyl;

$R^2$ and $R^3$, which are identical or different, represent a hydrogen atom or a ($C_1$-$C_4$)alkyl group, such as methyl;

$R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) by a hydroxyl group; particularly, $R^4$ is a hydrogen atom;

Z represents a CH group or a nitrogen atom, preferentially CH;

$Q^-$ is an anionic counterion as defined above, in particular a halide, such as chloride, or an alkyl sulfate, such as methyl sulfate, or mesityl.

In particular, the dyes of formulae (II-1) and (IV-1) are chosen from Basic Red 51, Basic Yellow 87 and Basic Orange 31 or their derivatives:

Basic Red 51

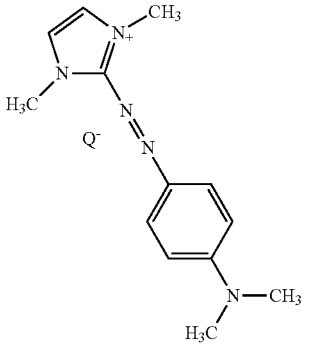

Basic Orange 31

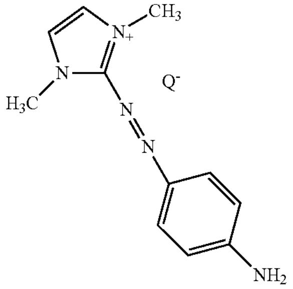

Basic Yellow 87

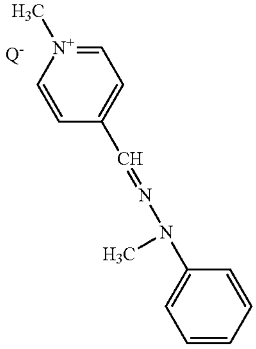

with Q' an anionic counterion as defined above, in particular a halide, such as chloride, or an alkyl sulfate, such as methyl sulfate, or mesityl.

Fluorescent Dyes

The direct dyes can be chosen from fluorescent direct dyes.

Mention may be made, by way of example of fluorescent dyes which can be used in the present invention, of neutral, anionic or cationic dyes chosen from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), diketopyrrolopyrroles, fluorindines, (poly)methines (in particular cyanines and styryls/hemicyanines), naphthalimides, naphthanilides, naphthylamines (such as dansyls), oxadiazoles, oxazines, perilones, perinones, perylenes, polyenes/carotenoids, squaranes, stilbenes and xanthenes.

Mention may also be made of the fluorescent dyes described in the documents EP 1 133 975, WO 03/029359, EP 860 636, WO 95/01772, WO 95/15144 and EP 714 954 and those listed in the encyclopedia "The Chemistry of Synthetic Dyes" by K. Venkataraman, 1952, Academic Press, Vol. 1 to 7, in the "Kirk-Othmer Encyclopedia of Chemical Technology", in the chapter "Dyes and Dye Intermediates", 1993, Wiley & Sons, and in various chapters of "Ullmann's Encyclopedia of Industrial Chemistry", 7th edition, Wiley & Sons, and in the handbook—"A Guide to Fluorescent Probes and Labeling Technologies", 10th Ed., Molecular Probes/Invitrogen—Oregon 2005, circulated on the Internet or in the preceding printed editions.

According to a preferred alternative form, the fluorescent dye(s) are cationic polymethines and comprise at least one quaternary ammonium group, such as those of following formula (Vb): $W^{+}—[C(R_c)═C(R_d)]_{m'}—ArQ^{-}$ in which formula (Vb):

$W^+$ represents a cationic heterocyclic or heteroaryl group, particularly comprising a quaternary ammonium optionally substituted by one or more $(C_1\text{-}C_8)$alkyl groups optionally substituted in particular by one or more hydroxyl groups;

Ar represents an aryl group, such as phenyl or naphthyl, which are optionally substituted, preferentially by i) one or more halogen atoms, such as chlorine or fluorine; ii) one or more $(C_1\text{-}C_8)$alkyl, preferably $(C_1\text{-}C_4)$ alkyl, groups, such as methyl; iii) one or more hydroxyl groups; iv) one or more $(C_1\text{-}C_8)$alkoxy groups, such as methoxy; v) one or more hydroxy$(C_1\text{-}C_8)$alkyl groups, such as hydroxyethyl, vi) one or more amino or (di)$(C_1\text{-}C_8)$alkylamino groups, preferably with the alkyl part $C_1\text{-}C_4$, optionally substituted by one or more hydroxyl groups, such as (di)hydroxyethylamino, vii) one or more acylamino groups; viii) one or more heterocycloalkyl groups, such as piperazinyl, piperidinyl or 5- or 6-membered heteroaryl, such as pyrrolidinyl, pyridinyl and imidazolinyl;

m' represents an integer ranging from 1 to 4; preferably, m' is equal to 1 or 2; more preferentially, m'=1;

$R_c$ and $R_d$, which are identical or different, represent a hydrogen atom or an optionally substituted $(C_1\text{-}C_8)$ alkyl group, preferably an optionally substituted $(C_1\text{-}C_4)$alkyl group, or alternatively $R_c$ contiguous with $W^+$ and/or $R_d$ contiguous with Ar form, with the atoms which carry them, a (hetero)cycloalkyl; in particular, $R_c$ is contiguous with $W^+$ and they form a (hetero) cycloalkyl, such as cyclohexyl;

$Q^-$ is an anionic counterion as defined above.

Anionic Dyes

The direct dyes can be chosen from anionic direct dyes or dyes commonly referred to as "acid" direct dyes for their affinity for alkaline substances.

The term "anionic direct dyes" is understood to mean any direct dye comprising in its structure at least one $CO_2R$ or $SO_3R$ substituent with R denoting a hydrogen atom or a cation originating from a metal or from an amine, or an ammonium ion. The anionic dyes can be chosen from acid nitro direct dyes, acid azo dyes, acid azine dyes, acid triarylmethane dyes, acid indoamine dyes, acid anthraquinone dyes, indigoids and acid natural dyes.

Preferably, the anionic direct dyes are acidic anthraquinones.

The direct dyes can be anionic direct dyes preferably chosen from the dyes of following formulae (III), (III'), (IV), (IV'), (V), (V'), (VI), (VI'), (VII), (VIII), (IX) and (X) and their mixtures:

a) The Diaryl Anionic Azo Dyes of Formula (III) or (III'):

(III)

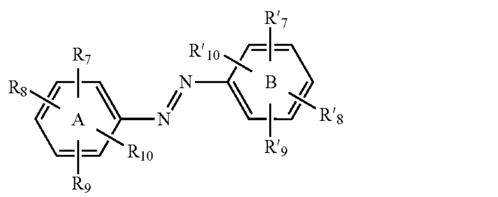

(III')

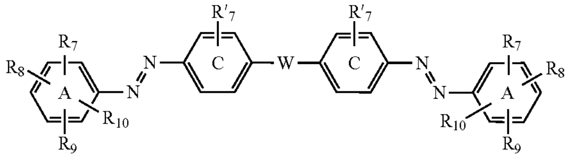

in which formulae (III) and (III'):

$R_7$, $R_8$, $R_9$, $R_{10}$, $R'_7$, $R'_9$ and $R'_{10}$, which are identical or different, represent a hydrogen atom or a group chosen from:

($C_1$-$C_6$)alkyl;

($C_1$-$C_6$)alkoxy, ($C_1$-$C_6$)alkylthio;

hydroxyl, mercapto;

nitro, nitroso;

R°—C(X)—X'—, R°—X'—C(X)—, R°—X'—C(X)—X"— with R° representing a hydrogen atom or a ($C_1$-$C_6$)alkyl or aryl group, such as phenyl; X, X' and X", which are identical or different, representing an oxygen or sulfur atom or NR with R representing a hydrogen atom or a ($C_1$-$C_6$)alkyl group;

$M^+(O)_2S(O^-)$—, with $M^+$ representing a hydrogen atom or a cationic counterion;

$M^+(O)CO^-$— with $M^+$ as defined above;

R"—$S(O)_2$—, with R" representing a hydrogen atom or an alkyl, aryl, (di)($C_1$-$C_6$)(alkyl)amino or aryl($C_1$-$C_6$)(alkyl)amino group; preferentially a phenylamino or phenyl group;

R'"—$S(O)_2$—X'— with R'" representing a ($C_1$-$C_6$) alkyl group or an aryl group which is optionally substituted, and X' as defined above;

(di)($C_1$-$C_6$)(alkyl)amino;

aryl($C_1$-$C_6$)(alkyl)amino, optionally substituted by one or more group(s) chosen from i) nitro; ii) nitroso; iii) $M^+(O)_2S(O^-)$— and iv) ($C_1$-$C_6$)alkoxy, with $M^+$ as defined above;

optionally substituted heteroaryl; preferentially a benzothiazolyl group;

cycloalkyl; in particular cyclohexyl;

Ar—N═N—, with Ar representing an optionally substituted aryl group; preferentially, a phenyl optionally substituted by one or more alkyl, $M^+(O)_2S(O^-)$— or phenylamino group(s);

or else two contiguous groups, $R_7$ with $R_8$ or $R_8$ with $R_9$ or $R_9$ with $R_{10}$, together form a fused benzo group A'; and $R'_7$ with $R'_8$ or $R'_8$ with $R'_9$ or $R'_9$ with $R'_{10}$, together form a fused benzo group B'; with A' and B' optionally substituted by one or more group(s) chosen from i) nitro; ii) nitroso; iii) $M^+(O)_2S(O^-)$—; iv) hydroxyl; v) mercapto; vi) (di)(alkyl)amino; vii) R°—C(X)—X'—; viii) R°—X'—C(X)—; ix) R°—X'—C(X)—X"—; x) Ar—N═N— and xi) aryl ($C_1$-$C_6$)(alkyl)amino which is optionally substituted; with $M^+$, R°, X, X', X" and Ar as defined above;

W represents a sigma a bond, an oxygen or sulfur atom or a divalent group i) —NR— with R as defined above, or ii) methylene —$C(R_a)(R_b)$—, with $R_a$ and $R_b$, which are identical or different, representing a hydrogen atom or an aryl group, or else $R_a$ and $R_b$ form, together with the carbon atom which carries them, a spirocycloalkyl; preferentially, W represents a sulfur atom or $R_a$ and $R_b$ together form a cyclohexyl;

it being understood that the formulae (III) and (III') comprise, on one of the rings A, A', B, B' or C:

at least one $M'^+(O)_2S(O^-)$— group, with $M'^+$ representing a cationic counterion; or at least one $M'^+(O)CO^-$— group, with $M'^+$ representing a cationic counterion;

preferably at least one sodium sulfonate group.

Mention may be made, as examples of dyes of formula (III), of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment Red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food Yellow 3 or Sunset Yellow;

and mention may be made, as examples of dyes of formula (III'), of: Acid Red 111, Acid Red 134 or Acid Yellow 38;

b) The Pyrazolone Anionic Azo Dyes of Formula (IV) or (IV'):

(IV)

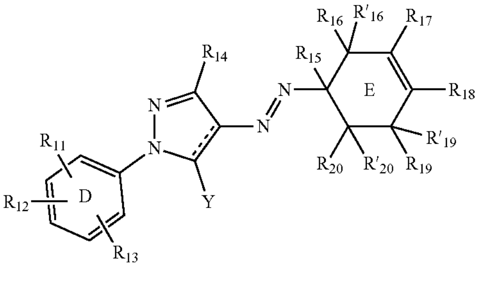

-continued (IV')

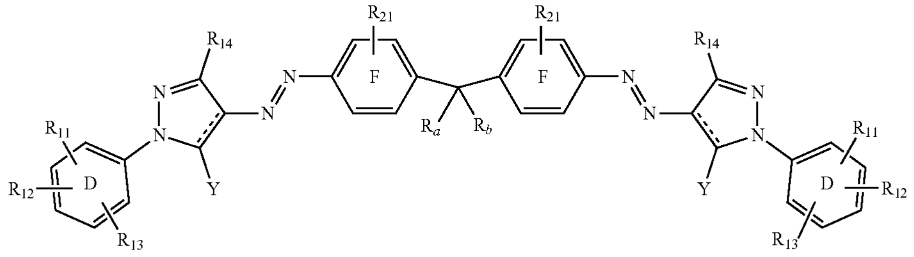

in which formulae (IV) and (IV'):

$R_{11}$, $R_{12}$ and $R_{13}$, which are identical or different, represent a hydrogen atom, a halogen atom, a $(C_1\text{-}C_6)$alkyl group or a $M^+(O)_2S(O^-)$— group, with $M^+$ as defined above;

$R_{14}$ represents a hydrogen atom, a $(C_1\text{-}C_6)$alkyl group or an $M^+C(O)O^-$— group, with $M^+$ as defined above;

$R_{15}$ represents a hydrogen atom;

$R_{16}$ represents an oxo group, in which case $R'_{16}$ is absent, or else $R_{15}$ with $R_{16}$ together form a double bond;

$R_{17}$ and $R_{18}$, which are identical or different, represent a hydrogen atom or a group chosen from:

$M^+(O)_2S(O^-)$—, with $M^+$ as defined above;

Ar—O—$S(O)_2$—, with Ar representing an optionally substituted aryl group; preferentially a phenyl optionally substituted by one or more alkyl group(s);

$R_{19}$ and $R_{20}$ together form either a double bond or an optionally substituted benzo group D';

$R'_{16}$, $R'_{19}$ and $R'_{20}$, which are identical or different, represent a hydrogen atom, a $(C_1\text{-}C_6)$alkyl group or a hydroxyl group;

$R_{21}$ represents a hydrogen atom, a $(C_1\text{-}C_6)$alkyl group or a $(C_1\text{-}C_6)$alkoxy group;

$R_a$ and $R_b$, which are identical or different, are as defined above; preferentially, $R_a$ represents a hydrogen atom and $R_b$ represents an aryl group, such as phenyl;

Y represents either a hydroxyl group or an oxo group;

- - - - represents a single bond when Y is an oxo group and represents a double bond when Y represents a hydroxyl group;

it being understood that the formulae (IV) and (IV') comprise, on one of the rings D or E:

at least one $M'^+(O)_2S(O^-)$— group, with representing a cationic counterion; or at least one $M'^+(O)CO^-$— group, with representing a cationic counterion;

preferably at least one sodium sulfonate group.

Mention may be made, as examples of dyes of formula (IV), of: Acid Red 195, Acid Yellow 23, Acid Yellow 27 or Acid Yellow 76, and mention may be made, as examples of dyes of formula (IV'), of: Acid Yellow 17;

c) The Anthraquinone Dyes of Formula (V) or (V'):

(V)

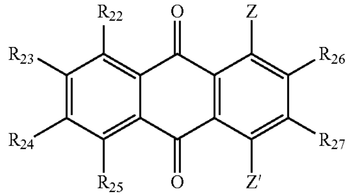

-continued (V')

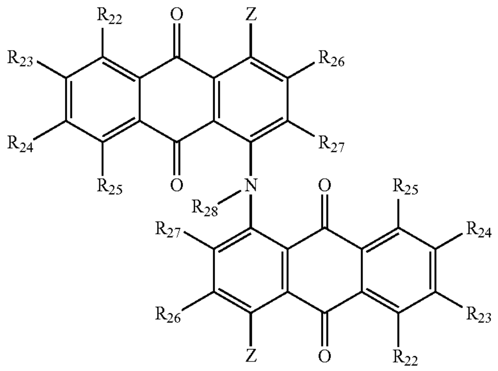

in which formulae (V) and (V'):

$R_{22}$, $R_{23}$, $R_{24}$, $R_{25}$, $R_{26}$ and $R_{27}$, which are identical or different, represent a hydrogen atom, a halogen atom or a group chosen from:

$(C_1\text{-}C_6)$alkyl;

hydroxyl, mercapto;

$(C_1\text{-}C_6)$alkoxy, $(C_1\text{-}C_6)$alkylthio;

optionally substituted aryloxy or arylthio, preferentially substituted by one or more groups chosen from alkyl and $M^+(O)_2S(O^-)$—, with $M^+$ as defined above;

aryl$(C_1\text{-}C_6)$(alkyl)amino optionally substituted by one or more group(s) chosen from alkyl and $M^+(O)_2S(O^-)$—, with $M^+$ as defined above;

(di)$(C_1\text{-}C_6)$(alkyl)amino;

(di)(hydroxy$(C_1\text{-}C_6)$alkyl)amino;

$M^+(O)_2S(O^-)$—, with $M^+$ as defined above;

Z' represents a hydrogen atom or an $NR_{28}R_{29}$ group with $R_{28}$ and $R_{29}$, which are identical or different, representing a hydrogen atom or a group chosen from:

$(C_1\text{-}C_6)$alkyl;

polyhydroxy$(C_1\text{-}C_6)$alkyl, such as hydroxyethyl;

aryl optionally substituted by one or more group(s), particularly i) $(C_1\text{-}C_6)$alkyl, such as methyl, n-dodecyl or n-butyl; ii) $M^+(O)_2S(O^-)$—, with $M^+$ as defined above; iii) R°—C(X)—X'—, R°—X'—C(X)— or R°—X'—C(X)—X"—, with R°, X, X' and X" as defined above; preferentially, R° represents a $(C_1\text{-}C_6)$alkyl group;

cycloalkyl, in particular cyclohexyl;

Z represents a group chosen from hydroxyl and $NR'_{28}R'_{29}$ with $R'_{28}$ and $R'_{29}$, which are identical or different, representing the same atoms or groups as $R_{28}$ and $R_{29}$ as defined above;

it being understood that the formulae (V) and (V') comprise:

at least one $M'^{+}(O)_2S(O^-)$— group, with representing a cationic counterion; or at least one $M'^{+}(O)CO^-$— group, with representing a cationic counterion;

preferably at least one sodium sulfonate group.

Mention may be made, as examples of dyes of formula (V), of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3 or Ext. Violet No. 2;

and mention may be made, as examples of dyes of formula (V'), of: Acid Black 48;

d) The Nitro Dyes of Formula (VI) or (VI'):

(VI)

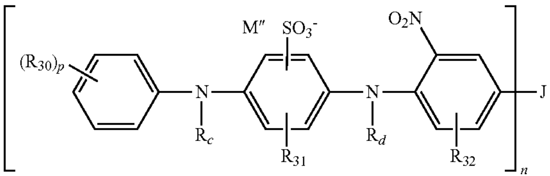

(VI')

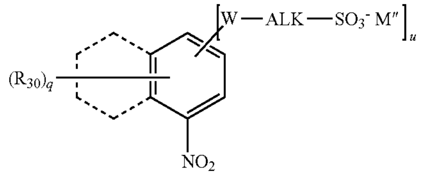

in which formulae (VI) and (VI'):

$R_{30}$, $R_{31}$ and $R_{32}$, which are identical or different, represent a hydrogen atom, a halogen atom or a group chosen from:

($C_1$-$C_6$)alkyl;

($C_1$-$C_6$)alkoxy optionally substituted by one or more hydroxyl group(s) or ($C_1$-$C_6$)alkylthio optionally substituted by one or more hydroxyl group(s);

hydroxyl, mercapto;

nitro, nitroso;

polyhalo($C_1$-$C_6$)alkyl;

R°—C(X)—X'—, R°—X'—C(X)— or R°—X'—C(X)—X"—, with R°, X, X' and X" as defined above;

$M^{+}(O)_2S(O^-)$—, with $M^+$ as defined above;

$M^{+}(O)CO^-$—, with $M^+$ as defined above;

(di)($C_1$-$C_6$)(alkyl)amino;

(di)(hydroxy($C_1$-$C_6$)alkyl)amino;

heterocycloalkyl, such as piperidino, piperazino or morpholino;

in particular, $R_{30}$, $R_{31}$ and $R_{32}$ represent a hydrogen atom;

$R_c$ and $R_d$, which are identical or different, represent a hydrogen atom or a ($C_1$-$C_6$)alkyl group;

W is as defined above; W represents in particular an —N(H)— group;

ALK represents a linear or branched divalent $C_1$-$C_6$ alkylene group; in particular, ALK represents a —$CH_2$—$CH_2$— group;

n has a value of 1 or 2;

p represents an integer ranging from 1 to 5;

q represents an integer ranging from 1 to 4;

u has a value of 0 or 1;

when n has a value of 1, J represents a nitro or nitroso group; in particular a nitro group;

when n has a value of 2, J represents an oxygen or sulfur atom or a divalent —$S(O)_m$— group with m representing an integer which is 1 or 2; preferentially, J represents an —$SO_2$— group;

M" represents a hydrogen atom or a cationic counterion;

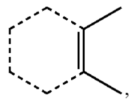

which is present or absent, represents a benzo group optionally substituted by one or more $R_{30}$ groups as defined above;

it being understood that the formulae (VI) and (VI') comprise:

at least one $M'^{+}(O)_2S(O^-)$— group, with representing a cationic counterion; or at least one $M'^{+}(O)CO^-$— group, with $M'^+$ representing a cationic counterion;

preferably at least one sodium sulfonate group.

Mention may be made, as examples of dyes of formula (VI), of: Acid Brown 13 and Acid Orange 3; mention may be made, as examples of dyes of formula (VI'), of: Acid Yellow 1, sodium salt of 2,4-dinitro-1-naphthol-7-sulfonic acid, 2-piperidino-5-nitrobenzenesulfonic acid, 2-(4'-N,N-(2"-hydroxyethyl)amino-2'-nitro)anilineethanesulfonic acid, 4-β-hydroxyethylamino-3-nitrobenzenesulfonic acid and Ext. D&C Yellow 7;

e) The Triarylmethane Dyes of Formula (VII):

(VII)

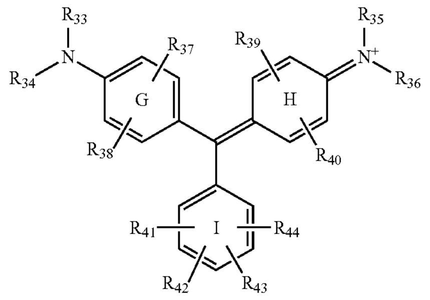

in which formula (VII):

$R_{33}$, $R_{34}$, $R_{35}$ and $R_{36}$, which are identical or different, represent a hydrogen atom or a group chosen from ($C_1$-$C_6$)alkyl, optionally substituted aryl and optionally substituted aryl($C_1$-$C_6$)alkyl; particularly a ($C_1$-$C_6$)alkyl group and benzyl group optionally substituted by an $M^{+}(O)_mS(O^-)$— group, with $M^+$ and m as defined above;

$R_{37}$, $R_{38}$, $R_{39}$, $R_{40}$, $R_{41}$, $R_{42}$, $R_{43}$ and $R_{44}$, which are identical or different, represent a hydrogen atom or a group chosen from:

($C_1$-$C_6$)alkyl;

($C_1$-$C_6$)alkoxy, ($C_1$-$C_6$)alkylthio;

(di)($C_1$-$C_6$)(alkyl)amino;

hydroxyl, mercapto;

nitro, nitroso;

R°—C(X)—X'—, R°—X'—C(X)— or R°—X'—C(X)—X"—, with R° representing a hydrogen atom, an alkyl group or aryl group and X, X' and X", which are identical or different, representing an oxygen or sulfur atom or NR with R representing a hydrogen atom or a $(C_1-C_6)$alkyl group;

$M^+(O)_2S(O^-)$—, with $M^+$ representing a hydrogen atom or a cationic counterion;

$M^+(O)CO^-$—, with $M^+$ as defined above;

or else two contiguous groups, $R_{41}$ with $R_{42}$ or $R_{42}$ with $R_{43}$ or $R_{43}$ with $R_{44}$, together form a fused benzo group optionally substituted by one or more group(s) chosen from i) nitro; ii) nitroso; iii) $M^+(O)_2S(O^-)$—; iv) hydroxyl; v) mercapto; vi) (di)$(C_1-C_6)$(alkyl) amino; vii) R°—C(X)—X'—; viii) R°—X'—C (X)—; ix) R°—X'—C(X)—X"—; with $M^+$, R°, X, X' and X" as defined above; in particular, $R_{37}$ to $R_{40}$ represent a hydrogen atom and $R_{41}$ to $R_{44}$, which are identical or different, represent a hydroxyl or $M^+(O)_2S(O^-)$— group with $M^+$ as defined above; and, when $R_{43}$ with $R_{44}$ together form a benzo group, it is preferentially substituted by an $(O)_2S(O^-)$— group;

it being understood that at least one of the rings G, H or I comprises:

at least one $M'^+(O)_2S(O^-)$— group, with $M'^+$ representing a cationic counterion; or at least one $M'^+(O)CO^-$— group, with $M'^+$ representing a cationic counterion; preferably at least one sodium sulfonate group.

Mention may be made, as examples of dyes of formula (VII), of: Acid Blue 1, Acid Blue 3, Acid Blue 7, Acid Blue 9, Acid Violet 49, Acid Green 3, Acid Green 5 and Acid Green 50.

f) The Xanthene-Based Dyes of Formula (VIII):

(VIII)

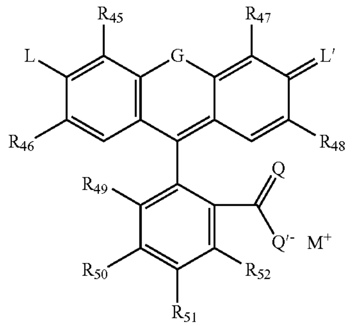

in which formula (VIII):

$R_{45}$, $R_{46}$, $R_{47}$ and $R_{48}$, which are identical or different, represent a hydrogen atom or a halogen atom;

$R_{49}$, $R_{50}$, $R_{51}$ and $R_{52}$, which are identical or different, represent a hydrogen atom, a halogen atom or a group chosen from:

$(C_1-C_6)$alkyl;

$(C_1-C_6)$alkoxy, $(C_1-C_6)$alkylthio;

hydroxyl, mercapto;

nitro, nitroso;

$M^+(O)_2S(O^-)$—, with $M^+$ representing a hydrogen atom or a cationic counterion;

$M^+(O)CO^-$—, with $M^+$ as defined above;

in particular, $R_{53}$, $R_{54}$, $R_{55}$ and $R_{48}$ represent a hydrogen atom or a halogen atom;

G represents an oxygen or sulfur atom or an $NR_e$ group, with $R_e$ as defined above; in particular, G represents an oxygen atom;

L represents an alkoxide $M^+O^-$, a thioalkoxide $M^+S^-$ or an $NR_f$ group, with $R_f$ representing a hydrogen atom or a $(C_1-C_6)$alkyl group and $M^+$ as defined above; $M^+$ is in particular sodium or potassium;

L' represents an oxygen or sulfur atom or an ammonium group: $N^+R_fR_g$, with $R_f$ and $R_g$, which are identical or different, representing a hydrogen atom, a $(C_1-C_6)$alkyl group or an aryl group which is optionally substituted; L' represents in particular an oxygen atom or a phenylamino group optionally substituted by one or more alkyl or $M^+(O)_mS(O^-)$— group(s), with m and $M^+$ as defined above;

Q and Q', which are identical or different, represent an oxygen or sulfur atom; in particular, Q and Q' represent an oxygen atom;

$M^+$ is as defined above.

Mention may be made, as examples of dyes of formula (VIII), of: Acid Yellow 73, Acid Red 51, Acid Red 52, Acid Red 87, Acid Red 92, Acid Red 95 and Acid Violet 9;

g) The Indole-Based Dyes of Formula (IX):

(IX)

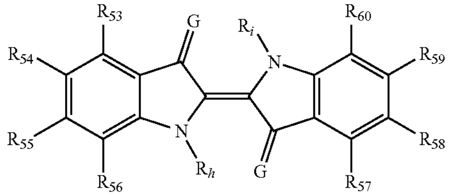

in which formula (IX):

$R_{53}$, $R_{54}$, $R_{55}$, $R_{56}$, $R_{57}$, $R_{58}$, $R_{59}$ and $R_{60}$, which are identical or different, represent a hydrogen atom or a group chosen from:

$(C_1-C_6)$alkyl;

$(C_1-C_6)$alkoxy, $(C_1-C_6)$alkylthio;

hydroxyl, mercapto;

nitro, nitroso;

R°—C(X)—X'—, R°—X'—C(X)— or R°—X'—C (X)—X"—, with R° representing a hydrogen atom, an alkyl group or aryl group and X, X' and X", which are identical or different, representing an oxygen or sulfur atom or NR with R representing a hydrogen atom or a $(C_1-C_6)$alkyl group;

$M^+(O)_2S(O^-)$—, with $M^+$ representing a hydrogen atom or a cationic counterion;

$M^+(O)CO^-$—, with $M^+$ as defined above;

G represents an oxygen or sulfur atom or an $NR_e$ group, with $R_e$ as defined above; in particular, G represents an oxygen atom;

$R_i$ and $R_h$, which are identical or different, represent a hydrogen atom or a $(C_1-C_6)$alkyl group;

it being understood that the formula (IX) comprises:

at least one $M'^+(O)_2S(O^-)$— group, with $M'^+$ representing a cationic counterion; or at least one $M'^+(O)CO^-$— group, with $M'^+$ representing a cationic counterion;

preferably at least one sodium sulfonate group.

Mention may be made, as example of dyes of formula (IX), of: Acid Blue 74.

h) The Quinoline-Based Dyes of Formula (X):

(X)

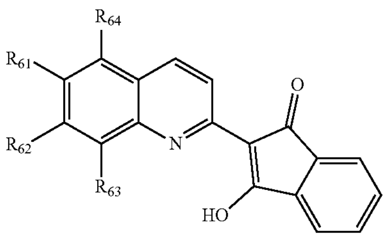

in which formula (X):

$R_{61}$ represents a hydrogen or halogen atom or a ($C_1$-$C_6$) alkyl group;

$R_{62}$, $R_{63}$ and $R_{64}$, which are identical or different, represent a hydrogen atom or an $M^+(O)_2S(O^-)$— group, with $M^+$ representing a hydrogen atom or a cationic counterion; or else $R_{61}$ with $R_{62}$ or $R_{61}$ with $R_{64}$ together form a benzo group optionally substituted by one or more $M^+(O)_2S(O^-)$— groups, with $M^+$ representing a hydrogen atom or a cationic counterion;

it being understood that the formula (X) comprises at least one $M'^+(O)_2S(O^-)$— group, with $M'^+$ representing a cationic counterion, preferably at least one sodium sulfonate group. Mention may be made, as examples of dyes of formula (X), of: Acid Yellow 2, Acid Yellow 3 and Acid Yellow 5.

More particularly, the dyes of formulae (III) to (VIII) of use in the invention are chosen from: Acid Red 87 (VIII) (C.I. 45380); Sodium salt of 2,4-dinitro-1-naphthol-7-sulfonic acid (VI') (C.I. 10316); Acid Orange 3 (VI) (C.I. 10383); Acid Yellow 9/Food Yellow 2 (III) (C.I. 13015); Direct Red 45/Food Red 13 (III) (C.I. 14780); Acid Black 52 (III) (C.I. 13711); Acid Yellow 36 (III) (C.I. 13065); Sodium salt of 1-hydroxy-2-(2',4'-xylyl-5-sulfonatoazo)naphthalene-4-sulfonic acid/Food Red 1 (III) (C.I. 14700); Acid Red 14/Food Red 3/Mordant Blue 79 (III) (C.I. 14720); Sodium salt of 4-hydroxy-3-[(2-methoxy-5-nitrophenyl)diaza]-6-(phenylamino)naphthalene-2-sulfonic acid/Acid Brown 4 (III) (C.I. 14805); Acid Orange 7/Pigment Orange 17/Solvent Orange 49 (III) (C.I. 15510); Food Yellow 3/Pigment Yellow 104 (III) (C.I. 15985); Acid Red 27/Food Red 9 (III) (C.I. 16185); Acid Orange 10/Food Orange 4 (III) (C.I. 16230); Acid Red 44 (III) (C.I. 16250); Acid Red 33/Food Red 12 (III) (C.I. 17200); Acid Red 184 (III) (C.I. 15685); Acid Violet 3 (III) (C.I. 19125); Sodium salt of 1-hydroxy-2-(4'-acetamidophenylazo)-8-acetamidonaphthalene-3,6-disulfonic acid/Acid Violet 7/Food Red 11 (III) (C.I. 18055); Acid Red 135 (III) (C.I. 18130); Acid Yellow 27 (IV) (C.I. 19130); Acid Yellow 23/Food Yellow 4 (IV) (C.I. 19140); 4'-(Sulfonato-2",4"-dimethyl)bis(2,6-phenylazo)-1,3-dihydroxybenzene/Acid Orange 24 (III) (C.I. 20170); Sodium salt of 1-amino-2-(4'-nitrophenylazo)-7-phenylazo-8-hydroxynaphthalene-3,6-disulfonic acid/Acid Black 1 (III) (C.I. 20470); (4-((4-Methylphenyl)sulfonyloxy)phenylazo)-2,2'-dimethyl-4-((2-hydroxy-5,8-disulfonato)naphthylazo) biphenyl/Acid Red 111 (III') (C.I. 23266); Food Black 2 (III) (C.I. 27755); 1-(4'-Sulfonatophenylazo)-4-((2"-hydroxy-3"-acetylamino-6",8"-disulfonato)naphthylazo)-6-sulfonatonaphthalene (tetrasodium salt)/Food Black 1 (III) (C.I. 25440); Acid Blue 9 (VII) (C.I. 42090); Acid Violet 43 (V) (C.I. 60730); Acid Green 25 (V) (C.I. 61570); Sodium salt of 1-amino-4-cyclohexylamino-9,10-anthraquinone-2-sulfonic acid/Acid Blue 62 (V) (C.I. 62045); Acid Blue 78 (V) (C.I. 62105); Sodium salt of 4-hydroxy-3-((2-methoxyphenyl)azo)-1-naphthalenesulfonic acid/Acid Red 4 (III) (C.I. 14710); 2-Piperidino-5-nitrobenzenesulfonic acid (VI'); 2-(4'-N,N-(2"-hydroxyethyl)amino-2'-nitro)anilineethanesulfonic acid (VI'); 4-β-hydroxyethylamino-3-nitrobenzenesulfonic acid (VI'); Acid Violet 49 (VII) (C.I. 42640); Acid Blue 7 (VII) (C.I. 42080); Sodium salt of 1,2-dihydroxy-3-sulfoanthraquinone/Mordant Red 3 (V) (C.I. 58005); Sodium salt of 1-amino-9,10-dihydro-9,10-dioxo-4-(phenylamino)-2-anthracenesulfonic acid/Acid Blue 25 (V) (C.I. 62055); Sodium salt of 4-hydroxy-3-((2-methoxyphenyl)azo)-1-naphthalenesulfonic acid/Acid Red 4 (III) (C.I. 14710).

Most of these dyes are described in particular in the Colour Index published by The Society of Dyers and Colourists, P.O. Box 244, Perkin House, 82 Grattan Road, Bradford, Yorkshire, BD12 JBN, England.

The anionic dyes which are most particularly preferred are the dyes designated in the Colour Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl) amino]-5-methylbenzenesulfonic acid), C.I. 15510 (monosodium salt of 4-[(2-hydroxy-1-naphthalenyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl[(3-sulfophenyl)methyl]amino] phenyl](2-sulfophenyl)methylene]-2,5-cyclohexadien-1-ylidene]-3-sulfobenzenemethanaminium hydroxide, internal salt), C.I. 61570 (disodium salt of 2,2'-[(9,10-dihydro-9,10-dioxo-1,4-anthracenediyl)diimino]bis[5-methylbenzenesulfonic acid]).

Use may also be made of the compounds corresponding to the mesomeric or tautomeric forms of the structures (III) to (X).

Natural Dyes

The direct dyes can be chosen from natural direct dyes.

Mention may be made, among the natural direct dyes which can be used according to the invention, of lawsone, juglone, alizarin, purpurin, carminic acid, kermesic acid, purpurogallin, protocatechaldehyde, indigo, isatin, curcumin, spinulosin, apigenidin, orceins, brazilin, brazilein, haematein or hematoxylin. Use may also be made of extracts or decoctions containing these natural dyes and in particular henna-based poultices or extracts.

According to a preferred embodiment, the direct dyes are chosen from the triarylmethane direct dyes of following formulae ($IIa_1$) and ($IIa_2$) and their mixtures:

($IIa_1$)

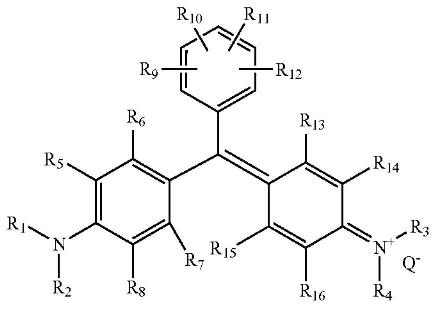

-continued (IIa$_2$)

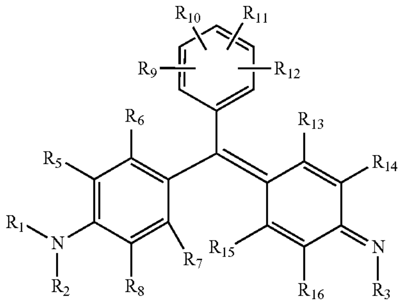

in which:

$R_1$, $R_2$, $R_3$ and $R_4$, which are identical or different, represent a hydrogen atom or a group from among: $(C_1\text{-}C_6)$alkyl which is optionally substituted, preferably by a hydroxyl group; aryl, such as phenyl, aryl$(C_1\text{-}C_4)$ alkyl, such as benzyl, heteroaryl or heteroaryl$(C_1\text{-}C_4)$ alkyl, or else two $R_1$ and $R_2$ and/or $R_3$ and $R_4$ groups, carried by the same nitrogen atom, form, together with the nitrogen atom which carries them, an optionally substituted heterocycloalkyl group, such as morpholino, piperazino or piperidino; preferably, $R_1$, $R_2$, $R_3$ and $R_4$, which are identical or different, represent a hydrogen atom or a $(C_1\text{-}C_4)$alkyl group;

$R_5$, $R_6$, $R_7$, $R_8$, $R_9$, $R_{10}$, $R_{11}$, $R_{12}$, $R_{13}$, $R_{14}$, $R_{15}$ and $R_{16}$, which are identical or different, represent a hydrogen atom, a halogen atom or a group chosen from i) hydroxyl, ii) thiol, iii) amino, iv) (di)$(C_1\text{-}C_4)$(alkyl) amino, v) (di)arylamino, such as (di)phenylamino, vi) nitro, vii) acylamino (—NR—C(O)R'), in which the R radical is a hydrogen atom or a $C_1\text{-}C_4$ alkyl radical optionally carrying at least one hydroxyl group and the R' radical is a $C_1\text{-}C_2$ alkyl radical; viii) carbamoyl ($(R)_2N$—C(O)—), in which the R radicals, which are identical or different, represent a hydrogen atom or a $C_1\text{-}C_4$ alkyl radical optionally carrying at least one hydroxyl group; ix) carboxylic acid or ester (—O—C(O)R') or (—C(O)OR'), in which the R' radical is a hydrogen atom or $C_1\text{-}C_4$ alkyl optionally carrying at least one hydroxyl group and the R' radical is a $C_1\text{-}C_2$ alkyl radical; x) alkyl which is optionally substituted, in particular by a hydroxyl group; xi) alkylsulfonylamino ($R'SO_2$—NR—), in which the R radical represents a hydrogen atom or a $C_1\text{-}C_4$ alkyl radical optionally carrying at least one hydroxyl group and the R' radical represents a $C_1\text{-}C_4$ alkyl radical or a phenyl radical; xii) aminosulfonyl ($(R)_2N$—$SO_2$—), in which the R radicals, which are identical or different, represent a hydrogen atom or a $C_1\text{-}C_4$ alkyl radical optionally carrying at least one hydroxyl group; xiii) $(C_1\text{-}C_4)$alkoxy; and xiv) $(C_1\text{-}C_4)$alkylthio;

or else two radicals carried by two contiguous carbon atoms, $R_5$ and $R_6$ and/or $R_7$ and $R_8$ and/or $R_9$ and $R_{10}$ and/or $R_{11}$ and $R_{12}$ and/or $R_{13}$ and $R_{14}$ and/or $R_{15}$ and $R_{16}$, form, together with the carbon atoms which carry them, a fused 6-membered aryl or heteroaryl, preferably benzo, ring, it being possible for said ring in addition to optionally be substituted, preferably an unsubstituted benzo ring;

$Q^-$ represents an anionic counterion for achieving electrical neutrality, preferably chosen from halides, such as chloride or bromide, and phosphate.

Preferably, the direct dye(s) are chosen from neutral direct dyes, cationic direct dyes and their mixtures.

More preferentially, the direct dye(s) are preferably chosen from Basic Red 51, HC Blue 15 and their mixtures.

The direct dye(s) can be present in the composition in a total content ranging from 0.001% to 5% by weight, preferably from 0.01% to 3% by weight, more preferentially from 0.1% to 1% by weight, more preferentially still from 0.1% to 0.5% by weight, with respect to the total weight of the composition.

The composition can additionally comprise one or more oxidation dyes.

Oxidation Dyes

The oxidation dyes are generally chosen from one or more oxidation bases optionally combined with one or more coupling agents (also known as couplers).

Oxidation Bases

The composition can optionally comprise one or more oxidation bases advantageously chosen from those conventionally used in the dyeing of keratin fibres.

By way of example, the oxidation bases are chosen from para-phenylenediamines, bis(phenyl)alkylenediamines, para-aminophenols, ortho-aminophenols and heterocyclic bases, and the corresponding addition salts.

The para-phenylenediamines which may be mentioned include, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N, N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(β-hydroxyethyl)-para-phenylenediamine, N—(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine and the corresponding addition salts with an acid.

Preference is in particular given, among the abovementioned para-phenylenediamines, to para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the corresponding addition salts with an acid.

The bis(phenyl)alkylenediamines which may be mentioned include, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N, N'-bis(4'-amino-3'-methylphenyl) ethylenediamine and 1,8-bis(2,5-diaminophenoxy)-3,6-dioxaoctane and the corresponding addition salts.

The para-aminophenols which are mentioned include, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethyl phenol, 4-amino-2-aminomethylphenol, 4-amino-2-(β-hydroxyethylaminomethyl)phenol and 4-amino-2-fluorophenol and the corresponding addition salts with an acid.

The ortho-aminophenols which may be mentioned include, for example, 2-aminophenol, 2-amino-5-methylphenol, 2-amino-6-methylphenol and 5-acetamido-2-aminophenol and the corresponding addition salts.

The heterocyclic bases which may be mentioned include, for example, pyridine, pyrimidine and pyrazole derivatives.

The pyridine derivatives which may be mentioned include the compounds for example described in Patents GB 1 026 978 and GB 1 153 196, for example 2,5-diaminopyridine, 2-(4-methoxyphenyl)amino-3-aminopyridine and 3,4-diaminopyridine and the corresponding addition salts.

Other pyridine oxidation bases which are of use in the present invention are the 3-aminopyrazolo[1,5-a]pyridine oxidation bases or the corresponding addition salts described, for example, in Patent Application FR 2 801 308. Examples which may be mentioned comprise pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl) ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino] ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases which are of use in the present invention are chosen from 3-aminopyrazolo[1,5-a]pyridines which are preferably substituted on the 2 carbon atom by:

a) a (di)($C_1$-$C_6$)(alkyl)amino group, it being possible for said alkyl group to be substituted by at least one hydroxyl, amino or imidazolium group;

b) an optionally cationic 5- to 7-membered heterocycloalkyl group containing from 1 to 3 heteroatoms, optionally substituted by one or more ($C_1$-$C_6$)alkyl groups, such as a di($C_1$-$C_4$)alkylpiperazinium group; or c) a ($C_1$-$C_6$)alkoxy group optionally substituted by one or more hydroxyl groups, such as a β-hydroxyalkoxy group, and the corresponding addition salts.

The pyrimidine derivatives which may be mentioned include the compounds described, for example, in Patents DE 2359399, JP 88-169571, JP 05-63124 and EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

The pyrazole derivatives which may be mentioned include the compounds described in Patents DE 3843892 and DE 4133957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole and the corresponding addition salts. Use may also be made of 4,5-diamino-1-(β-methoxyethyl)pyrazole.

A 4,5-diaminopyrazole will preferably be used and more preferentially still 4,5-diamino-1-(β-hydroxyethyl)pyrazole and/or a corresponding salt.

The pyrazole derivatives which may also be mentioned comprise diamino-N,N-dihydropyrazolopyrazolones and in particular those described in Patent Application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or a corresponding salt.

Coupling Agents

The composition can optionally comprise one or more coupling agents advantageously chosen from those conventionally used in the dyeing of keratin fibres.

Mention may in particular be made, among these coupling agents, of meta-phenylenediamines, meta-aminophenols, meta-diphenols, naphthalene-based coupling agents and heterocyclic coupling agents, and also the corresponding addition salts. Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N—(β-hydroxyethyl)amino-3,4-methylenedioxybenzene, 2,6-bis(β-hydroxyethylamino)toluene, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole, 6-methylpyrazolo[1,5-a]benzimidazole, 2-methyl-5-aminophenol, 5-N—(β-hydroxyethyl)amino-2-methylphenol, 3-aminophenol and 3-amino-2-chloro-6-methylphenol, the corresponding addition salts with an acid and the corresponding mixtures.

In general, the addition salts of oxidation bases and of coupling agents which can be used in the context of the invention are chosen in particular from the addition salts with an acid, such as the hydrochlorides, hydrobromides, sulfates, citrates, succinates, tartrates, lactates, tosylates, benzenesulfonates, phosphates and acetates.

The oxidation base(s) each advantageously represent(s) from 0.001% to 10% by weight, with respect to the total weight of the composition, and preferably from 0.005% to 5% by weight, with respect to the total weight of the composition.

The coupling agent(s), if they are present, each advantageously represent(s) from 0.001% to 10% by weight, with respect to the total weight of the composition, and preferably from 0.005% to 5% by weight, with respect to the total weight of the composition.

Additional Basifying Agents

The composition can also comprise one or more additional basifying agents other than the carbonates, bicarbonates and silicates as defined above.

According to a preferred embodiment, the composition according to the invention does not comprise an additional alkaline agent chosen from aqueous ammonia and/or alkanolamines.

Acidifying Agents

The composition can additionally comprise one or more acidifying agents.

pH of the Composition

The composition according to the invention preferably exhibits a pH of less than or equal to 11, preferably of less than or equal to 10.5, preferably of less than or equal to 10.

The pH of the composition according to the invention can vary from 8 to 11, preferably from 8 to 10.5, more preferentially from 8 to 10.

According to a particularly preferred embodiment, the pH of the composition according to the invention varies from 8.3 to 10.

Other Characteristics of the Composition

The composition preferably comprises water in a content ranging from 5% to 99% by weight, more preferentially ranging from 5% to 80% by weight, with respect to the total weight of the composition.

The composition can additionally comprise at least one organic solvent.

The term "organic solvent" is understood to mean an organic substance which is capable of dissolving another substance without chemically modifying it.

The composition according to the invention can be provided in liquid form, in the form of a serum, in thickened form, in particular a gel, a cream, a wax or a paste, or in foam form.

The composition according to the invention can also comprise one or more additional compounds chosen from non-ionic, anionic, cationic or amphoteric surfactants, cationic, anionic, non-ionic or zwitterionic, associative or non-associative, thickening polymers of natural or synthetic origin, silicones in the form of oils, gums or resins or non-silicone vegetable, mineral or synthetic oils, UV-screening agents, fillers, such as pearlescent agents and metal oxides, such as titanium dioxides, clays, fragrances, peptizing agents, vitamins and preservatives.

Process for Simultaneous Bleaching and Dyeing of Keratin Fibres

According to a second aspect, a subject-matter of the present invention is a process for simultaneous bleaching and dyeing of keratin fibres, comprising the application, to the keratin fibres, of a composition as defined above.

In particular, the composition is applied to wet or dry keratin fibres.

Preferably, the keratin fibres are dark keratin fibres.

The term "dark keratin fibres" is understood to mean keratin fibres, the height of tone of which is less than or equal to 6 (dark blond) and preferably less than or equal to 4 (chestnut).

The "height of tone" is the unit known to hairstyling professionals and published in the work *Science des traitements capillaires* [The Science of Hair Care] by Charles Zviak, 1988, published by Masson, pages 215 and 278; the heights of tone range, according to the European scale, from 1 (black) to 10 (light light blond), one unit corresponding to one tone; the higher the figure, the lighter the shade.

The composition can advantageously be applied to the keratin fibres in an amount ranging from 0.1 g to 20 g of composition per gram of keratin fibres.

The composition is left to stand on the fibres for a period of time, generally from 1 minute to 1 hour, preferably from 5 minutes to 60 minutes.

By way of example, the composition can be left to stand on the fibres for a period of time of 50 minutes.

The composition can be left to stand on the fibres under an occlusive system. Mention may be made, as non-limiting example of an occlusive system, of an occlusive system of wrapper type made of aluminium or plastic film or hair cap type, with or without holes.

The temperature during the simultaneous bleaching and dyeing process is conventionally between ambient temperature (between 15° C. and 25° C.) and 80° C., preferably between ambient temperature and 60° C.

By way of example, the temperature during the simultaneous bleaching and dyeing process is 33° C.

On conclusion of the treatment, the keratin fibres are optionally rinsed with water, optionally washed with a shampoo and then rinsed with water, before being dried or left to dry naturally.

The drying stage can be carried out using absorbent paper, a hairdryer or a styling hood.

The composition according to the invention is preferably prepared by mixing at least two compositions. Preferably, the mixing of said at least two compositions is carried out extemporaneously, before the application of the composition according to the invention to the keratin fibres.

According to a preferred embodiment, the composition according to the invention results from the mixing of two compositions (A) and (B1):

a composition (A) comprising i) one or more chemical oxidizing agents chosen from hydrogen peroxide, hydrogen peroxide-generating systems other than peroxygenated salts and their mixtures as defined above; and a composition (B1) comprising:

ii) one or more compounds chosen from carbonates, carbonate-generating systems, bicarbonates, bicarbonate-generating systems and their mixtures as defined above; and iii) one or more silicates as defined above; and iv) one or more direct dyes as defined above;

or from the mixing of three compositions (A), (B2) and (C):

a composition (A) comprising i) one or more chemical oxidizing agents chosen from hydrogen peroxide, hydrogen peroxide-generating systems other than peroxygenated salts and their mixtures as defined above; and a composition (B2) comprising:

ii) one or more compounds chosen from carbonates, carbonate-generating systems, bicarbonates, bicarbonate-generating systems and their mixtures as defined above; and iii) one or more silicates as defined above; and a composition (C) comprising iv) one or more direct dyes as defined above.

Preferably, at least one of the compositions (A) or (B1) or at least one of the three compositions (A) or (B2) or (C) is aqueous. More preferentially, the composition (A) is aqueous.

According to a specific embodiment, the composition (B1) or (B2) is anhydrous.

The term "aqueous composition" is understood to mean a composition comprising at least 5% by weight of water. Preferably, an aqueous composition comprises more than 10% by weight of water and more advantageously still more than 20% by weight of water.

According to a more preferred embodiment, the composition according to the invention results from the mixing of two compositions (A') and (B1'):

a composition (A') comprising i) hydrogen peroxide; and a composition (B1') comprising:

ii) one or more compounds chosen from carbonates, bicarbonates and their mixtures as defined above; and iii) one or more silicates as defined above; and iv) one or more direct dyes as defined above;

or from the mixing of three compositions (A'), (B2') and (C'):

a composition (A') comprising i) hydrogen peroxide; and a composition (B2') comprising:

ii) one or more compounds chosen from carbonates, bicarbonates and their mixtures as defined above; and iii) one or more silicates as defined above; and a composition (C') comprising iv) one or more direct dyes as defined above.

Preferably, at least one of the compositions (A') or (B1') or at least one of the three compositions (A') or (B2') or (C') is aqueous. More preferentially, the composition (A') is aqueous.

According to a specific embodiment, the composition (B1') or (B2') is anhydrous.

Use

According to a third aspect, a subject-matter of the present invention is the use of the composition as defined above for the simultaneous bleaching and dyeing of keratin fibres.

Multi-Compartment Device (Kit)

According to a fourth aspect, a subject-matter of the present invention is a multi-compartment device (kit) comprising:

a first compartment including a composition (A) as defined above; and a second compartment including a composition (B1) as defined above;

or a first compartment including a composition (A) as defined above; and a second compartment including a composition (B2) as defined above; and a third compartment including a composition (C) as defined above.

Preferably, the multi-compartment device comprises:

a first compartment including a composition (A') as defined above; and a second compartment including a composition (B1') as defined above;

or a first compartment including a composition (A') as defined above; and a second compartment including a composition (B2') as defined above; and a third compartment including a composition (C') as defined above.

EXAMPLES

The examples which follow make possible a better understanding of the invention without, however, exhibiting a limiting nature. In the examples which follow, unless otherwise indicated, all the amounts are shown as percentages by weight, with respect to the total weight of the composition.

Example 1

The following compositions C1 and C2 were prepared and then applied according to the application protocol described below:

TABLE 1

| Ingredients | C1 | C2 |
|---|---|---|
| Oxidizing cream Blond Studio 40 Vol. L'Oréal Professionnel (12% of $H_2O_2$) | 70.0 (i.e. 8.4 of $H_2O_2$) | 70.0 (i.e. 8.4 of $H_2O_2$) |
| Sodium silicate (CAS: 1344-09-8) | 10 | 10 |
| Ammonium bicarbonate | 10 | 10 |
| HC Blue 15 | 0.5 | — |
| Basic Red 51 | — | 0.5 |
| Water | q.s. for 100 | q.s. for 100 |

Application Protocol 10 g of each of the compositions C1 and C2 are applied to 2 locks of 1 g of dark hair of HT4 Caucasian type on a hot plate maintained at a temperature of 33° C. Everything is covered with a cellophane film for 50 min.

The locks are subsequently rinsed, washed with a standard shampoo, rinsed again and then dried.

Results

TABLE 2

| Composition | Hair colour observed |
|---|---|
| C1 | Vivid blue |
| C2 | Vivid red |

The compositions according to the invention make it possible to simultaneously bleach and dye dark hair in a single stage and make it possible to obtain vivid colours.

The invention claimed is:

1. A composition, comprising:

i) at least one chemical oxidizing agent chosen from hydrogen peroxide, hydrogen peroxide-generating systems other than peroxygenated salts, or mixtures of two or more thereof;

ii) at least one compound chosen from carbonates, carbonate-generating systems, bicarbonates, bicarbonate-generating systems, or mixtures of two or more thereof;

iii) at least one silicate; and iv) at least one direct dye;

wherein the composition is devoid of persulfates.

2. The composition of claim 1, wherein the chemical oxidizing agent is chosen from hydrogen peroxide.

3. The composition of claim 1, wherein the total amount of chemical oxidizing agent(s) ranges from 1% to 12% by weight, relative to the total weight of the composition.

4. The composition of claim 1, wherein the total amount of (bi)carbonates(s) chosen from carbonates, carbonate-generating systems, bicarbonates, bicarbonate-generating systems, or mixtures of two or more thereof ranges from 0.01% to 20% by weight, relative to the total weight of the composition.

5. The composition of claim 1, wherein the at least one compound chosen from carbonates, carbonate-generating systems, bicarbonates, bicarbonate-generating systems, or mixtures of two or more thereof is chosen from carbonates, carbonate-generating systems, or mixtures of two or more thereof.

6. The composition of claim 5, wherein the total amount of carbonate(s), carbonate-generating system(s), or mixtures of two or more thereof ranges from 0.01% to 20% by weight, relative to the total weight of the composition.

7. The composition of claim 5, wherein the carbonates are chosen from:

alkali metal carbonates;

alkaline earth metal carbonates;

lanthanide carbonates;

transition metal carbonates;

bismuth carbonate;

cadmium carbonate;

thallium carbonate;

zinc carbonate;

compounds of formula $(N^+R^1R^2R^3R^4)_2CO_3^{2-}$, wherein $R^1$, $R^2$, $R^3$, and $R^4$ are independently chosen from a hydrogen atom or a $(C_1\text{-}C_4)$ alkyl group optionally substituted by a hydroxyl group;

guanidine carbonate; or mixtures of two or more thereof.

8. The composition of claim 1, wherein the at least one compound chosen from carbonates, carbonate-generating systems, bicarbonates, bicarbonate-generating systems, or mixtures of two or more thereof is chosen from bicarbonates, bicarbonate-generating systems, or mixtures of two or more thereof.

9. The composition of claim 8, wherein the total amount of bicarbonate(s), bicarbonate-generating system(s), or mixtures of two or more thereof ranges from 0.01% to 20% by weight, relative to the total weight of the composition.

10. The composition of claim 8, wherein the bicarbonate(s) are chosen from:

alkali metal bicarbonates;

alkaline earth metal bicarbonates;

compounds of formula $N^+R^1R^2R^3R^4HCO_3^-$, wherein $R^1$, $R^2$, $R^3$, and $R^4$ are independently chosen from a hydrogen atom or a $(C_1\text{-}C_4)$ alkyl group optionally substituted by a hydroxyl group;

aminoguanidine bicarbonate;

or mixtures of two or more thereof.

11. The composition of claim 1, wherein the at least one silicate is chosen from alkali metal silicates, alkaline earth metal silicates, aluminum silicates, trimethylammonium silicates, or mixtures of two or more thereof.

12. The composition of claim 1, wherein the total amount of silicate(s) ranges from 1% to 40% by weight, relative to the total weight of the composition.

13. The composition of claim 8, wherein the weight ratio of the total amount of (bi)carbonate(s), (bi)carbonate-generating system(s), or mixtures of two or more thereof to the total amount of silicate(s) ranges from 0.001 to 100.

14. The composition of claim 8, wherein the weight ratio of the total amount of (bi)carbonate(s), (bi)carbonate-generating system(s), or mixtures of two or more thereof to the total amount of chemical oxidizing agent(s) ranges from 0.01 to 20.

15. The composition of claim 1, wherein the composition comprises:

at least one carbonate(s), carbonate-generating system(s), or mixtures of two or more thereof; and at least one bicarbonate(s), bicarbonate-generating system(s), or mixtures of two or more thereof, wherein weight ratio of the total amount of carbonate(s), carbonate-generating system(s), or mixtures of two or more thereof to the total amount of bicarbonate(s), bicarbonate-generating system(s), or mixtures of two or more thereof ranges from 0.01 to 100.

16. The composition of claim 1, wherein the pH of the composition ranges from 8 to 11.

17. The composition of claim 1, wherein the at least one direct dye is chosen from neutral direct dyes, cationic direct dyes, anionic direct dyes, or mixtures of two or more thereof.

18. The composition of claim 1, wherein the total amount of direct dye(s) ranges from 0.001% to 5% by weight, relative to the total weight of the composition.

19. A method comprising:

(a) mixing a composition (A) with a composition (B1), or (b) mixing the composition (A), a composition (B2), and a composition (C), wherein the composition (A) comprises:

i) at least one chemical oxidizing agent chosen from hydrogen peroxide, hydrogen peroxide-generating systems other than peroxygenated salts, or mixtures of two or more thereof, wherein the composition (A) is devoid of persulfates;

wherein the composition (B1) comprises:
- ii) at least one compound chosen from carbonates, carbonate-generating systems, bicarbonates, bicarbonate-generating systems, or mixtures of two or more thereof;
- iii) at least one silicate; and
- iv) at least one direct dye;

wherein the composition (B2) comprises:
- ii) at least one compound chosen from carbonates, carbonate-generating systems, bicarbonates, bicarbonate-generating systems, or mixtures of two or more thereof; and
- iii) at least one silicate, and wherein the composition (C) comprises iv) at least one direct dye.

20. A kit comprising:

a first compartment comprising a composition (A) comprising:
- i) at least one chemical oxidizing agent chosen from hydrogen peroxide, hydrogen peroxide-generating systems other than peroxygenated salts, or mixtures of two or more thereof, wherein the composition (A) is devoid of persulfates; and a second compartment comprising a composition (B) comprising:
- ii) at least one compound chosen from carbonates, carbonate-generating systems, bicarbonates, bicarbonate-generating systems, or mixtures of two or more thereof;
- iii) at least one silicate; and
- iv) optionally at least one direct dye; and wherein the kit optionally comprises a composition (C) comprising iv) at least one direct dye.

* * * * *